United States Patent
Elimelech et al.

(10) Patent No.: US 12,290,416 B2
(45) Date of Patent: May 6, 2025

(54) REGISTRATION OF A FIDUCIAL MARKER FOR AN AUGMENTED REALITY SYSTEM

(71) Applicant: AUGMEDICS LTD., Yokneam Illit (IL)

(72) Inventors: Nissan Elimelech, Beerotaim (IL); Stuart Wolf, Yokneam (IL)

(73) Assignee: AUGMEDICS LTD., Yokneam Illit (IL)

( * ) Notice: Subject to any disclaimer, the term of this patent is extended or adjusted under 35 U.S.C. 154(b) by 0 days.

(21) Appl. No.: 18/632,588

(22) Filed: Apr. 11, 2024

(65) Prior Publication Data

US 2024/0341911 A1    Oct. 17, 2024

Related U.S. Application Data

(63) Continuation of application No. 17/045,766, filed as application No. PCT/IB2019/053524 on Apr. 30, 2019, now Pat. No. 11,980,507.

(60) Provisional application No. 62/665,541, filed on May 2, 2018.

(51) Int. Cl.
*A61B 8/00* (2006.01)
*A61B 34/20* (2016.01)
*A61B 90/00* (2016.01)

(52) U.S. Cl.
CPC .............. *A61B 90/39* (2016.02); *A61B 34/20* (2016.02); *A61B 2034/2055* (2016.02); *A61B 2090/365* (2016.02); *A61B 2090/3916* (2016.02); *A61B 2090/3937* (2016.02); *A61B 2090/3966* (2016.02); *A61B 2090/3983* (2016.02);
(Continued)

(58) Field of Classification Search
CPC .............. A61B 90/39; A61B 2090/365; A61B 2090/3916; A61B 2090/3937; A61B 2090/3966; A61B 2090/3983; A61B 2090/3991; A61B 2090/3995
See application file for complete search history.

(56) References Cited

U.S. PATENT DOCUMENTS

| | | | |
|---|---|---|---|
| 3,101,715 A | 8/1963 | Glassman | |
| 3,690,776 A | 9/1972 | Zaporoshan | |
| 4,459,358 A | 7/1984 | Berke | |

(Continued)

FOREIGN PATENT DOCUMENTS

| | | |
|---|---|---|
| CN | 103106348 A | 5/2013 |
| CN | 105310756 A | 2/2016 |

(Continued)

OTHER PUBLICATIONS

16 Augmented Reality Glasses of 2021 (with Features), in Back to News, Dated May 6, 2022, accessed at https://web.archive.org/web/20221127195438/https://circuitstream.com/blog/16-augmented-reality-glasses-of-2021-with-features-breakdowns/.

(Continued)

*Primary Examiner* — Joel F Brutus
(74) *Attorney, Agent, or Firm* — KNOBBE, MARTENS, OLSON & BEAR, LLP

(57) ABSTRACT

A registration marker comprising a radiotransparent substrate and a pattern formed in at least two dimensions, which is disposed on the substrate and is optically visible. The registration marker also has a multiplicity of radiopaque elements, which are disposed in the substrate and are spatially arranged in at least two dimensions to provide a unique pattern.

18 Claims, 5 Drawing Sheets

(52) U.S. Cl.
CPC .................. *A61B 2090/3991* (2016.02); *A61B 2090/3995* (2016.02)

(56) References Cited

U.S. PATENT DOCUMENTS

| | | | |
|---|---|---|---|
| 4,711,512 A | 12/1987 | Upatnieks |
| 4,863,238 A | 9/1989 | Brewster |
| 4,944,739 A | 7/1990 | Torre |
| 5,100,420 A | 3/1992 | Green et al. |
| 5,147,365 A | 9/1992 | Whitlock et al. |
| 5,357,292 A | 10/1994 | Wiedner |
| 5,410,802 A | 5/1995 | Buckley |
| 5,441,042 A | 8/1995 | Putman |
| 5,442,146 A | 8/1995 | Bell et al. |
| 5,510,832 A | 4/1996 | Garcia |
| D370,309 S | 5/1996 | Stucky |
| 5,620,188 A | 4/1997 | McCurry et al. |
| 5,636,255 A | 6/1997 | Ellis |
| 5,665,092 A | 9/1997 | Mangiardi et al. |
| 5,743,731 A | 4/1998 | Lares et al. |
| 5,771,121 A | 6/1998 | Hentschke |
| 5,792,046 A | 8/1998 | Dobrovolny |
| 5,841,507 A | 11/1998 | Barnes |
| 6,006,126 A | 12/1999 | Cosman |
| 6,038,467 A | 3/2000 | De Bliek et al. |
| 6,125,164 A | 9/2000 | Murphy et al. |
| 6,138,530 A | 10/2000 | McClure |
| 6,147,805 A | 11/2000 | Fergason |
| 6,227,667 B1 | 5/2001 | Halldorsson et al. |
| 6,256,529 B1 | 7/2001 | Holupka et al. |
| 6,285,505 B1 | 9/2001 | Melville et al. |
| 6,314,310 B1 | 11/2001 | Ben-Haim et al. |
| 6,349,001 B1 | 2/2002 | Spitzer |
| 6,444,192 B1 | 9/2002 | Mattrey |
| 6,447,503 B1 | 9/2002 | Wynne et al. |
| 6,449,090 B1 | 9/2002 | Omar et al. |
| 6,456,405 B2 | 9/2002 | Horikoshi et al. |
| 6,456,868 B2 | 9/2002 | Saito et al. |
| 6,474,159 B1 | 11/2002 | Foxlin et al. |
| 6,518,939 B1 | 2/2003 | Kikuchi |
| 6,527,777 B2 | 3/2003 | Justin |
| 6,529,331 B2 | 3/2003 | Massof et al. |
| 6,549,645 B1 | 4/2003 | Oikawa et al. |
| 6,578,962 B1 | 6/2003 | Amir et al. |
| 6,609,022 B2 | 8/2003 | Mlsmeier et al. |
| 6,610,009 B2 | 8/2003 | Person |
| D480,476 S | 10/2003 | Martinson et al. |
| 6,659,611 B2 | 12/2003 | Amir et al. |
| 6,675,040 B1 | 1/2004 | Cosman |
| 6,683,584 B2 | 1/2004 | Ronzani et al. |
| 6,690,964 B2 | 2/2004 | Bieger et al. |
| 6,714,810 B2 | 3/2004 | Grzeszczuk et al. |
| 6,737,425 B1 | 5/2004 | Yamamoto et al. |
| 6,740,882 B2 | 5/2004 | Weinberg |
| 6,757,068 B2 | 6/2004 | Foxlin |
| 6,759,200 B1 | 7/2004 | Stanton, Jr. |
| 6,847,336 B1 | 1/2005 | Lemelson et al. |
| 6,856,324 B2 | 2/2005 | Sauer et al. |
| 6,856,826 B2 | 2/2005 | Seeley et al. |
| 6,891,518 B2 | 5/2005 | Sauer et al. |
| 6,900,777 B1 | 5/2005 | Hebert et al. |
| 6,919,867 B2 | 7/2005 | Sauer |
| 6,921,167 B2 | 7/2005 | Nagata |
| 6,966,668 B2 | 11/2005 | Cugini et al. |
| 6,980,849 B2 | 12/2005 | Sasso |
| 6,993,374 B2 | 1/2006 | Sasso |
| 6,997,552 B1 | 2/2006 | Hung |
| 6,999,239 B1 | 2/2006 | Martins et al. |
| 7,000,262 B2 | 2/2006 | Bielefeld |
| 7,035,371 B2 | 4/2006 | Boese et al. |
| 7,043,961 B2 | 5/2006 | Pandey et al. |
| 7,072,435 B2 | 7/2006 | Metz et al. |
| 7,103,233 B2 | 9/2006 | Stearns |
| 7,107,091 B2 | 9/2006 | Jutras et al. |
| 7,112,656 B2 | 9/2006 | Desnoyers et al. |
| 7,141,812 B2 | 11/2006 | Appleby et al. |
| 7,157,459 B2 | 1/2007 | Ohta et al. |
| 7,169,785 B2 | 1/2007 | Timmer et al. |
| 7,171,255 B2 | 1/2007 | Holupka et al. |
| 7,176,936 B2 | 2/2007 | Sauer et al. |
| 7,187,792 B2 | 3/2007 | Fu et al. |
| 7,190,331 B2 | 3/2007 | Genc et al. |
| 7,194,295 B2 | 3/2007 | Vilsmeier |
| 7,215,322 B2 | 5/2007 | Genc et al. |
| 7,229,078 B2 | 6/2007 | Lechot |
| 7,231,076 B2 | 6/2007 | Fu et al. |
| 7,235,076 B2 | 6/2007 | Pacheco |
| 7,239,330 B2 | 7/2007 | Sauer et al. |
| 7,241,292 B2 | 7/2007 | Hooven |
| 7,259,266 B2 | 8/2007 | Carter et al. |
| 7,260,426 B2 | 8/2007 | Schweikard et al. |
| 7,269,192 B2 | 9/2007 | Hayashi |
| 7,281,826 B2 | 10/2007 | Huang |
| 7,315,636 B2 | 1/2008 | Kuduvalli |
| 7,320,556 B2 | 1/2008 | Vagn-Erik |
| 7,330,578 B2 | 2/2008 | Wang et al. |
| 7,359,535 B2 | 4/2008 | Salla et al. |
| 7,364,314 B2 | 4/2008 | Nilsen et al. |
| 7,366,934 B1 | 4/2008 | Narayan et al. |
| 7,379,077 B2 | 5/2008 | Bani-Hashemi et al. |
| 7,431,453 B2 | 10/2008 | Hogan |
| 7,435,219 B2 | 10/2008 | Kim |
| 7,450,743 B2 | 11/2008 | Sundar et al. |
| 7,458,977 B2 | 12/2008 | McGinley et al. |
| 7,462,852 B2 | 12/2008 | Appleby et al. |
| 7,493,153 B2 | 2/2009 | Ahmed et al. |
| 7,505,617 B2 | 3/2009 | Fu et al. |
| 7,507,968 B2 | 3/2009 | Wollenweber et al. |
| 7,518,136 B2 | 4/2009 | Appleby et al. |
| 7,525,735 B2 | 4/2009 | Sottilare et al. |
| D592,691 S | 5/2009 | Chang |
| D592,692 S | 5/2009 | Chang |
| D592,693 S | 5/2009 | Chang |
| 7,536,216 B2 | 5/2009 | Geiger et al. |
| 7,542,791 B2 | 6/2009 | Mire et al. |
| 7,556,428 B2 | 7/2009 | Sukovic et al. |
| 7,557,824 B2 | 7/2009 | Holliman |
| 7,563,228 B2 | 7/2009 | Ma et al. |
| 7,567,834 B2 | 7/2009 | Clayton et al. |
| 7,570,791 B2 | 8/2009 | Frank et al. |
| 7,586,686 B1 | 9/2009 | Hall |
| D602,620 S | 10/2009 | Cristoforo |
| 7,605,826 B2 | 10/2009 | Sauer |
| 7,606,613 B2 | 10/2009 | Simon et al. |
| 7,607,775 B2 | 10/2009 | Hermanson et al. |
| 7,620,223 B2 | 11/2009 | Xu et al. |
| 7,623,902 B2 | 11/2009 | Pacheco |
| 7,627,085 B2 | 12/2009 | Boyden et al. |
| 7,630,753 B2 | 12/2009 | Simon et al. |
| 7,633,501 B2 | 12/2009 | Wood et al. |
| 7,645,050 B2 | 1/2010 | Wilt et al. |
| 7,653,226 B2 | 1/2010 | Guhring et al. |
| 7,657,075 B2 | 2/2010 | Mswanathan |
| 7,689,019 B2 | 3/2010 | Boese et al. |
| 7,689,042 B2 | 3/2010 | Brunner et al. |
| 7,689,320 B2 | 3/2010 | Prisco et al. |
| 7,699,486 B1 | 4/2010 | Beiner |
| 7,699,793 B2 | 4/2010 | Goette et al. |
| 7,719,769 B2 | 5/2010 | Sugihara et al. |
| D617,825 S | 6/2010 | Chang |
| 7,734,327 B2 | 6/2010 | Colquhoun |
| D619,285 S | 7/2010 | Cristoforo |
| 7,751,865 B2 | 7/2010 | Jascob et al. |
| 7,758,204 B2 | 7/2010 | Klipstein et al. |
| 7,768,702 B2 | 8/2010 | Hirose et al. |
| 7,769,236 B2 | 8/2010 | Fiala |
| 7,773,074 B2 | 8/2010 | Arenson et al. |
| 7,774,044 B2 | 8/2010 | Sauer et al. |
| 7,822,483 B2 | 10/2010 | Stone et al. |
| D628,307 S | 11/2010 | Krause-Bonte |
| 7,826,902 B2 | 11/2010 | Stone et al. |
| 7,831,073 B2 | 11/2010 | Fu et al. |
| 7,831,096 B2 | 11/2010 | Williamson, Jr. |
| 7,835,778 B2 | 11/2010 | Foley et al. |

(56) References Cited

U.S. PATENT DOCUMENTS

| | | |
|---|---|---|
| 7,835,784 B2 | 11/2010 | Mire et al. |
| 7,837,987 B2 | 11/2010 | Shi et al. |
| 7,840,093 B2 | 11/2010 | Fu et al. |
| 7,840,253 B2 | 11/2010 | Tremblay et al. |
| 7,840,256 B2 | 11/2010 | Lakin et al. |
| 7,853,305 B2 | 12/2010 | Simon et al. |
| 7,854,705 B2 | 12/2010 | Pawluczyk et al. |
| 7,857,271 B2 | 12/2010 | Lees |
| 7,860,282 B2 | 12/2010 | Boese et al. |
| D630,766 S | 1/2011 | Harbin |
| 7,865,269 B2 | 1/2011 | Prisco et al. |
| 7,874,686 B2 | 1/2011 | Rossner et al. |
| 7,881,770 B2 | 2/2011 | Melkent et al. |
| 7,893,413 B1 | 2/2011 | Appleby et al. |
| 7,894,649 B2 | 2/2011 | Fu et al. |
| 7,920,162 B2 | 4/2011 | Masini et al. |
| 7,922,391 B2 | 4/2011 | Essenreiter et al. |
| 7,938,553 B1 | 5/2011 | Beiner |
| 7,945,310 B2 | 5/2011 | Gattani et al. |
| 7,953,471 B2 | 5/2011 | Clayton et al. |
| 7,969,383 B2 | 6/2011 | Eberl et al. |
| 7,974,677 B2 | 7/2011 | Mire et al. |
| 7,985,756 B2 | 7/2011 | Barlow et al. |
| 7,991,557 B2 | 8/2011 | Liew et al. |
| 7,993,353 B2 | 8/2011 | Roner et al. |
| 7,996,064 B2 | 8/2011 | Simon et al. |
| 8,004,524 B2 | 8/2011 | Deinzer |
| 8,021,300 B2 | 9/2011 | Ma et al. |
| 8,022,984 B2 | 9/2011 | Cheong et al. |
| 8,045,266 B2 | 10/2011 | Nakamura |
| 8,060,181 B2 | 11/2011 | Rodriguez et al. |
| 8,068,581 B2 | 11/2011 | Boese et al. |
| 8,068,896 B2 | 11/2011 | Daghighian et al. |
| 8,077,943 B2 | 12/2011 | Williams et al. |
| 8,079,957 B2 | 12/2011 | Ma et al. |
| 8,081,812 B2 | 12/2011 | Kreiser |
| 8,085,075 B2 | 12/2011 | Huffman et al. |
| 8,085,897 B2 | 12/2011 | Morton |
| 8,090,175 B2 | 1/2012 | Fu et al. |
| 8,092,400 B2 | 1/2012 | Warkentine et al. |
| 8,108,072 B2 | 1/2012 | Zhao et al. |
| 8,112,292 B2 | 2/2012 | Simon |
| 8,116,847 B2 | 2/2012 | Gattani et al. |
| 8,120,847 B2 | 2/2012 | Chang |
| 8,121,255 B2 | 2/2012 | Sugiyama |
| 8,155,479 B2 | 4/2012 | Hoffman et al. |
| 8,180,132 B2 | 5/2012 | Gorges et al. |
| 8,180,429 B2 | 5/2012 | Sasso |
| 8,208,599 B2 | 6/2012 | Ye et al. |
| 8,216,211 B2 | 7/2012 | Mathis et al. |
| 8,221,402 B2 | 7/2012 | Francischelli et al. |
| 8,239,001 B2 | 8/2012 | Verard et al. |
| 8,244,012 B2 | 8/2012 | Liang et al. |
| 8,253,778 B2 | 8/2012 | Atsushi |
| 8,271,069 B2 | 9/2012 | Jascob et al. |
| 8,280,491 B2 | 10/2012 | Kuduvalli et al. |
| 8,285,021 B2 | 10/2012 | Boese et al. |
| 8,300,315 B2 | 10/2012 | Kobayashi |
| 8,305,685 B2 | 11/2012 | Heine et al. |
| 8,306,305 B2 | 11/2012 | Porat et al. |
| 8,309,932 B2 | 11/2012 | Haselman et al. |
| 8,317,320 B2 | 11/2012 | Huang |
| 8,328,815 B2 | 12/2012 | Farr et al. |
| 8,335,553 B2 | 12/2012 | Rubner et al. |
| 8,335,557 B2 | 12/2012 | Maschke |
| 8,340,379 B2 | 12/2012 | Razzaque et al. |
| 8,369,925 B2 | 2/2013 | Giesel et al. |
| 8,386,022 B2 | 2/2013 | Jutras et al. |
| 8,394,144 B2 | 3/2013 | Zehavi et al. |
| 8,398,541 B2 | 3/2013 | Dimaio et al. |
| 8,444,266 B2 | 5/2013 | Waters |
| 8,457,719 B2 | 6/2013 | Moctezuma De La Barrera et al. |
| 8,467,851 B2 | 6/2013 | Mire et al. |
| 8,469,902 B2 | 6/2013 | Dick et al. |
| 8,475,470 B2 | 7/2013 | Von Jako |
| 8,494,612 B2 | 7/2013 | Vetter et al. |
| 8,509,503 B2 | 8/2013 | Nahum et al. |
| 8,511,827 B2 | 8/2013 | Hua et al. |
| 8,531,394 B2 | 9/2013 | Maltz |
| 8,540,364 B2 | 9/2013 | Waters |
| 8,545,012 B2 | 10/2013 | Waters |
| 8,548,567 B2 | 10/2013 | Maschke et al. |
| 8,556,883 B2 | 10/2013 | Saleh |
| 8,559,596 B2 | 10/2013 | Thomson et al. |
| 8,567,945 B2 | 10/2013 | Waters |
| 8,571,353 B2 | 10/2013 | Watanabe |
| 8,585,598 B2 | 11/2013 | Razzaque et al. |
| 8,600,001 B2 | 12/2013 | Schweizer |
| 8,600,477 B2 | 12/2013 | Beyar et al. |
| 8,605,199 B2 | 12/2013 | Imai |
| 8,611,988 B2 | 12/2013 | Miyamoto |
| 8,612,024 B2 | 12/2013 | Stone et al. |
| 8,634,897 B2 | 1/2014 | Simon et al. |
| 8,641,621 B2 | 2/2014 | Razzaque et al. |
| 8,643,950 B2 | 2/2014 | König |
| 8,644,907 B2 | 2/2014 | Hartmann et al. |
| 8,674,902 B2 | 3/2014 | Park et al. |
| 8,686,923 B2 | 4/2014 | Eberl et al. |
| 8,690,581 B2 | 4/2014 | Ruf et al. |
| 8,690,776 B2 | 4/2014 | Razzaque et al. |
| 8,692,845 B2 | 4/2014 | Fedorovskaya et al. |
| 8,693,632 B2 | 4/2014 | Allison |
| 8,694,075 B2 | 4/2014 | Groszmann et al. |
| 8,699,765 B2 | 4/2014 | Hao et al. |
| 8,705,829 B2 | 4/2014 | Frank et al. |
| 8,737,708 B2 | 5/2014 | Hartmann et al. |
| 8,746,887 B2 | 6/2014 | Shestak et al. |
| 8,764,025 B1 | 7/2014 | Gao |
| 8,784,450 B2 | 7/2014 | Moskowitz et al. |
| 8,786,689 B1 | 7/2014 | Liu |
| D710,545 S | 8/2014 | Wu |
| D710,546 S | 8/2014 | Wu |
| 8,827,934 B2 | 9/2014 | Chopra et al. |
| 8,831,706 B2 | 9/2014 | Fu et al. |
| 8,836,768 B1 | 9/2014 | Rafii et al. |
| 8,838,199 B2 | 9/2014 | Simon et al. |
| 8,848,977 B2 | 9/2014 | Bammer et al. |
| 8,855,395 B2 | 10/2014 | Baturin et al. |
| 8,878,900 B2 | 11/2014 | Yang et al. |
| 8,879,815 B2 | 11/2014 | Miao et al. |
| 8,885,177 B2 | 11/2014 | Ben-Yishai et al. |
| 8,890,772 B2 | 11/2014 | Woo et al. |
| 8,890,773 B1 | 11/2014 | Pederson |
| 8,890,943 B2 | 11/2014 | Lee et al. |
| 8,897,514 B2 | 11/2014 | Feikas et al. |
| 8,900,131 B2 | 12/2014 | Chopra et al. |
| 8,903,150 B2 | 12/2014 | Star-Lack et al. |
| 8,908,952 B2 | 12/2014 | Isaacs et al. |
| 8,911,358 B2 | 12/2014 | Koninckx et al. |
| 8,917,268 B2 | 12/2014 | Johnsen et al. |
| 8,920,776 B2 | 12/2014 | Gaiger et al. |
| 8,922,589 B2 | 12/2014 | Laor |
| 8,941,559 B2 | 1/2015 | Bar-Zeev et al. |
| 8,942,455 B2 | 1/2015 | Chou et al. |
| 8,950,877 B2 | 2/2015 | Northey et al. |
| 8,953,246 B2 | 2/2015 | Koenig |
| 8,961,500 B2 | 2/2015 | Dicorleto et al. |
| 8,965,583 B2 | 2/2015 | Ortmaier et al. |
| 8,969,829 B2 | 3/2015 | Wollenweber et al. |
| 8,989,349 B2 | 3/2015 | Thomson et al. |
| 8,992,580 B2 | 3/2015 | Bar et al. |
| 8,994,729 B2 | 3/2015 | Nakamura |
| 8,994,795 B2 | 3/2015 | Oh |
| 9,004,711 B2 | 4/2015 | Gerolemou |
| 9,005,211 B2 | 4/2015 | Brundobler et al. |
| 9,011,441 B2 | 4/2015 | Bertagnoli et al. |
| 9,057,759 B2 | 6/2015 | Klingenbeck et al. |
| 9,060,757 B2 | 6/2015 | Lawson et al. |
| 9,066,751 B2 | 6/2015 | Sasso |
| 9,081,436 B1 | 7/2015 | Berme et al. |
| 9,084,635 B2 | 7/2015 | Nuckley et al. |
| 9,085,643 B2 | 7/2015 | Svanborg et al. |
| 9,087,471 B2 | 7/2015 | Miao |
| 9,100,643 B2 | 8/2015 | McDowall et al. |

(56) References Cited

U.S. PATENT DOCUMENTS

| | | |
|---|---|---|
| 9,101,394 B2 | 8/2015 | Arata et al. |
| 9,104,902 B2 | 8/2015 | Xu et al. |
| 9,111,175 B2 | 8/2015 | Strommer et al. |
| 9,123,155 B2 | 9/2015 | Cunningham et al. |
| 9,125,556 B2 | 9/2015 | Zehavi et al. |
| 9,129,054 B2 | 9/2015 | Nawana et al. |
| 9,129,372 B2 | 9/2015 | Kriston et al. |
| 9,132,361 B2 | 9/2015 | Smithwick |
| 9,135,706 B2 | 9/2015 | Zagorchev et al. |
| 9,141,873 B2 | 9/2015 | Takemoto |
| 9,142,020 B2 | 9/2015 | Deguise et al. |
| 9,149,317 B2 | 10/2015 | Arthur et al. |
| 9,165,203 B2 | 10/2015 | McCarthy |
| 9,165,362 B2 | 10/2015 | Siewerdsen et al. |
| 9,179,984 B2 | 11/2015 | Teichman et al. |
| D746,354 S | 12/2015 | Chang |
| 9,208,916 B2 | 12/2015 | Appleby et al. |
| 9,220,573 B2 | 12/2015 | Kendrick et al. |
| 9,225,895 B2 | 12/2015 | Kozinski |
| 9,232,982 B2 | 1/2016 | Soler et al. |
| 9,235,934 B2 | 1/2016 | Mandella et al. |
| 9,240,046 B2 | 1/2016 | Carrell et al. |
| 9,244,278 B2 | 1/2016 | Sugiyama et al. |
| 9,247,240 B2 | 1/2016 | Park et al. |
| 9,259,192 B2 | 2/2016 | Ishihara |
| 9,265,572 B2 | 2/2016 | Fuchs et al. |
| 9,269,192 B2 | 2/2016 | Kobayashi |
| 9,283,052 B2 | 3/2016 | Rodriguez Ponce |
| 9,286,730 B2 | 3/2016 | Bar-Zeev et al. |
| 9,289,267 B2 | 3/2016 | Sauer et al. |
| 9,294,222 B2 | 3/2016 | Proctor, Jr. |
| 9,300,949 B2 | 3/2016 | Ahearn |
| 9,305,354 B2 | 4/2016 | Burlon et al. |
| 9,310,591 B2 | 4/2016 | Hua et al. |
| 9,320,474 B2 | 4/2016 | Demri et al. |
| 9,323,055 B2 | 4/2016 | Baillot |
| 9,330,477 B2 | 5/2016 | Rappel |
| 9,335,547 B2 | 5/2016 | Takano et al. |
| 9,335,567 B2 | 5/2016 | Nakamura |
| 9,341,704 B2 | 5/2016 | Picard et al. |
| 9,344,686 B2 | 5/2016 | Moharir |
| 9,349,066 B2 | 5/2016 | Koo et al. |
| 9,349,520 B2 | 5/2016 | Demetriou et al. |
| 9,364,294 B2 | 6/2016 | Razzaque et al. |
| 9,370,332 B2 | 6/2016 | Paladini et al. |
| 9,373,166 B2 | 6/2016 | Azar |
| 9,375,639 B2 | 6/2016 | Kobayashi et al. |
| 9,378,558 B2 | 6/2016 | Kajiwara et al. |
| 9,380,287 B2 | 6/2016 | Nistico et al. |
| 9,387,008 B2 | 7/2016 | Sarvestani et al. |
| 9,392,129 B2 | 7/2016 | Simmons |
| 9,395,542 B2 | 7/2016 | Tilleman et al. |
| 9,398,936 B2 | 7/2016 | Razzaque et al. |
| 9,400,384 B2 | 7/2016 | Griffith |
| 9,414,041 B2 | 8/2016 | Ko et al. |
| 9,424,611 B2 | 8/2016 | Kanjirathinkal et al. |
| 9,424,641 B2 | 8/2016 | Wiemker et al. |
| 9,427,286 B2 | 8/2016 | Siewerdsen et al. |
| 9,438,894 B2 | 9/2016 | Park et al. |
| 9,443,488 B2 | 9/2016 | Borenstein et al. |
| 9,453,804 B2 | 9/2016 | Tahtali |
| 9,456,878 B2 | 10/2016 | Macfarlane et al. |
| 9,465,235 B2 | 10/2016 | Chang |
| 9,468,373 B2 | 10/2016 | Larsen |
| 9,470,908 B1 | 10/2016 | Frankel et al. |
| 9,473,766 B2 | 10/2016 | Douglas et al. |
| 9,492,222 B2 | 11/2016 | Singh |
| 9,495,585 B2 | 11/2016 | Bicer et al. |
| 9,498,132 B2 | 11/2016 | Maier-Hein et al. |
| 9,498,231 B2 | 11/2016 | Haider et al. |
| 9,499,999 B2 | 11/2016 | Nanqing |
| 9,507,155 B2 | 11/2016 | Morimoto |
| 9,513,495 B2 | 12/2016 | Waters |
| 9,521,966 B2 | 12/2016 | Schwartz |
| 9,526,443 B1 | 12/2016 | Berme et al. |
| 9,530,382 B2 | 12/2016 | Simmons |
| 9,532,846 B2 | 1/2017 | Nakamura |
| 9,532,849 B2 | 1/2017 | Anderson et al. |
| 9,533,407 B1 | 1/2017 | Ragner |
| 9,538,962 B1 | 1/2017 | Hannaford et al. |
| 9,545,233 B2 | 1/2017 | Sirpad et al. |
| 9,546,779 B2 | 1/2017 | Rementer |
| 9,547,174 B2 | 1/2017 | Gao et al. |
| 9,547,940 B1 | 1/2017 | Sun et al. |
| 9,557,566 B2 | 1/2017 | Fujimaki |
| 9,560,318 B2 | 1/2017 | Reina et al. |
| 9,561,095 B1 | 2/2017 | Nguyen et al. |
| 9,561,446 B2 | 2/2017 | Brecher |
| 9,565,415 B2 | 2/2017 | Zhang et al. |
| 9,572,661 B2 | 2/2017 | Robin et al. |
| 9,576,398 B1 | 2/2017 | Zehner et al. |
| 9,576,556 B2 | 2/2017 | Simmons |
| 9,581,822 B2 | 2/2017 | Morimoto |
| 9,610,056 B2 | 4/2017 | Lavallee et al. |
| 9,612,657 B2 | 4/2017 | Bertram et al. |
| 9,626,936 B2 | 4/2017 | Bell |
| 9,629,595 B2 | 4/2017 | Walker et al. |
| 9,633,431 B2 | 4/2017 | Merlet |
| 9,645,395 B2 | 5/2017 | Bolas et al. |
| 9,646,423 B1 | 5/2017 | Sun et al. |
| 9,672,597 B2 | 6/2017 | Amiot et al. |
| 9,672,607 B2 | 6/2017 | Demri et al. |
| 9,672,640 B2 | 6/2017 | Kleiner |
| 9,675,306 B2 | 6/2017 | Morton |
| 9,675,319 B1 | 6/2017 | Razzaque et al. |
| 9,684,980 B2 | 6/2017 | Royalty et al. |
| 9,690,119 B2 | 6/2017 | Garofolo et al. |
| RE46,463 E | 7/2017 | Fienbloom et al. |
| 9,693,748 B2 | 7/2017 | Rai et al. |
| 9,710,968 B2 | 7/2017 | Dillavou et al. |
| 9,713,502 B2 | 7/2017 | Finkman et al. |
| 9,724,119 B2 | 8/2017 | Hissong et al. |
| 9,724,165 B2 | 8/2017 | Arata et al. |
| 9,726,888 B2 | 8/2017 | Giartosio et al. |
| 9,728,006 B2 | 8/2017 | Varga |
| 9,729,831 B2 | 8/2017 | Birnkrant et al. |
| 9,746,739 B2 | 8/2017 | Alton et al. |
| 9,757,034 B2 | 9/2017 | Desjardins et al. |
| 9,757,087 B2 | 9/2017 | Simon et al. |
| 9,766,441 B2 | 9/2017 | Rappel |
| 9,766,459 B2 | 9/2017 | Alton et al. |
| 9,767,608 B2 | 9/2017 | Lee et al. |
| 9,770,203 B1 | 9/2017 | Berme et al. |
| 9,772,102 B1 | 9/2017 | Ferguson |
| 9,772,495 B2 | 9/2017 | Tam et al. |
| 9,791,138 B1 | 10/2017 | Feinbloom et al. |
| 9,800,995 B2 | 10/2017 | Libin et al. |
| 9,805,504 B2 | 10/2017 | Zhang et al. |
| 9,808,148 B2 | 11/2017 | Miller et al. |
| 9,839,448 B2 | 12/2017 | Reckling et al. |
| 9,844,413 B2 | 12/2017 | Daon et al. |
| 9,851,080 B2 | 12/2017 | Wilt et al. |
| 9,858,663 B2 | 1/2018 | Penney et al. |
| 9,861,446 B2 | 1/2018 | Lang |
| 9,864,214 B2 | 1/2018 | Fass |
| 9,872,733 B2 | 1/2018 | Shoham et al. |
| 9,875,544 B2 | 1/2018 | Rai et al. |
| 9,877,642 B2 | 1/2018 | Duret |
| 9,885,465 B2 | 2/2018 | Nguyen |
| 9,886,552 B2 | 2/2018 | Dillavou et al. |
| 9,886,760 B2 | 2/2018 | Liu et al. |
| 9,892,564 B1 | 2/2018 | Cvetko et al. |
| 9,898,866 B2 | 2/2018 | Fuchs et al. |
| 9,901,414 B2 | 2/2018 | Lively et al. |
| 9,911,187 B2 | 3/2018 | Steinle et al. |
| 9,911,236 B2 | 3/2018 | Bar-Zeev et al. |
| 9,927,611 B2 | 3/2018 | Rudy et al. |
| 9,928,629 B2 | 3/2018 | Benishti et al. |
| 9,940,750 B2 | 4/2018 | Dillavou et al. |
| 9,943,374 B2 | 4/2018 | Merritt et al. |
| 9,947,110 B2 | 4/2018 | Haimerl |
| 9,952,664 B2 | 4/2018 | Border et al. |
| 9,956,054 B2 | 5/2018 | Aguirre-Valencia |
| 9,958,674 B2 | 5/2018 | Border |

(56) References Cited

U.S. PATENT DOCUMENTS

| | | |
|---|---|---|
| 9,959,620 B2 | 5/2018 | Merlet |
| 9,959,629 B2 | 5/2018 | Dillavou et al. |
| 9,965,681 B2 | 5/2018 | Border et al. |
| 9,968,297 B2 | 5/2018 | Connor |
| 9,980,780 B2 | 5/2018 | Lang |
| 9,986,228 B2 | 5/2018 | Woods |
| D824,523 S | 7/2018 | Paoli et al. |
| 10,010,379 B1 | 7/2018 | Gibby et al. |
| 10,013,531 B2 | 7/2018 | Richards et al. |
| 10,015,243 B2 | 7/2018 | Kazerani et al. |
| 10,016,243 B2 | 7/2018 | Esterberg |
| 10,022,064 B2 | 7/2018 | Kim et al. |
| 10,022,065 B2 | 7/2018 | Ben-Yishai et al. |
| 10,022,104 B2 | 7/2018 | Sell et al. |
| 10,023,615 B2 | 7/2018 | Bonny |
| 10,026,015 B2 | 7/2018 | Cavusoglu et al. |
| 10,034,713 B2 | 7/2018 | Yang et al. |
| 10,042,167 B2 | 8/2018 | McDowall et al. |
| 10,046,165 B2 | 8/2018 | Frewin et al. |
| 10,055,838 B2 | 8/2018 | Elenbaas et al. |
| 10,066,816 B2 | 9/2018 | Chang |
| 10,067,359 B1 | 9/2018 | Ushakov |
| 10,073,515 B2 | 9/2018 | Awdeh |
| 10,080,616 B2 | 9/2018 | Wilkinson et al. |
| 10,082,680 B2 | 9/2018 | Chung |
| 10,085,709 B2 | 10/2018 | Lavallee et al. |
| 10,105,187 B2 | 10/2018 | Corndorf et al. |
| 10,107,483 B2 | 10/2018 | Oren |
| 10,108,833 B2 | 10/2018 | Hong et al. |
| 10,123,840 B2 | 11/2018 | Dorman |
| 10,130,378 B2 | 11/2018 | Bryan |
| 10,132,483 B1 | 11/2018 | Feinbloom et al. |
| 10,134,166 B2 | 11/2018 | Benishti et al. |
| 10,134,194 B2 | 11/2018 | Kepner et al. |
| 10,139,652 B2 | 11/2018 | Windham |
| 10,139,920 B2 | 11/2018 | Isaacs et al. |
| 10,142,496 B1 | 11/2018 | Rao et al. |
| 10,151,928 B2 | 12/2018 | Ushakov |
| 10,154,239 B2 | 12/2018 | Casas |
| 10,159,530 B2 | 12/2018 | Lang |
| 10,163,207 B2 | 12/2018 | Merlet |
| 10,166,079 B2 | 1/2019 | McLachlin et al. |
| 10,175,507 B2 | 1/2019 | Nakamura |
| 10,175,753 B2 | 1/2019 | Boesen |
| 10,181,361 B2 | 1/2019 | Dillavou et al. |
| 10,186,055 B2 | 1/2019 | Takahashi et al. |
| 10,188,672 B2 | 1/2019 | Wagner |
| 10,194,131 B2 | 1/2019 | Casas |
| 10,194,990 B2 | 2/2019 | Amanatullah et al. |
| 10,194,993 B2 | 2/2019 | Roger et al. |
| 10,195,076 B2 | 2/2019 | Fateh |
| 10,197,803 B2 | 2/2019 | Badiali et al. |
| 10,197,816 B2 | 2/2019 | Waisman et al. |
| 10,207,315 B2 | 2/2019 | Appleby et al. |
| 10,212,517 B1 | 2/2019 | Beltran et al. |
| 10,230,719 B2 | 3/2019 | Vaughn et al. |
| 10,231,893 B2 | 3/2019 | Lei et al. |
| 10,235,606 B2 | 3/2019 | Miao et al. |
| 10,240,769 B1 | 3/2019 | Braganca et al. |
| 10,247,965 B2 | 4/2019 | Ton |
| 10,251,724 B2 | 4/2019 | McLachlin et al. |
| 10,261,324 B2 | 4/2019 | Chuang et al. |
| 10,262,424 B2 | 4/2019 | Ketcha et al. |
| 10,274,731 B2 | 4/2019 | Maimone |
| 10,278,777 B1 | 5/2019 | Lang |
| 10,292,768 B2 | 5/2019 | Lang |
| 10,296,805 B2 | 5/2019 | Yang et al. |
| 10,319,154 B1 | 6/2019 | Chakravarthula et al. |
| 10,326,975 B2 | 6/2019 | Casas |
| 10,332,267 B2 | 6/2019 | Rai et al. |
| 10,339,719 B2 | 7/2019 | Jagga et al. |
| 10,352,543 B1 | 7/2019 | Braganca et al. |
| 10,357,146 B2 | 7/2019 | Fiebel et al. |
| 10,357,574 B2 | 7/2019 | Hilderbrand et al. |
| 10,366,489 B2 | 7/2019 | Boettger et al. |
| 10,368,947 B2 | 8/2019 | Lang |
| 10,368,948 B2 | 8/2019 | Tripathi |
| 10,382,748 B2 | 8/2019 | Benishti et al. |
| 10,383,654 B2 | 8/2019 | Yilmaz et al. |
| 10,386,645 B2 | 8/2019 | Abou Shousha |
| 10,388,076 B2 | 8/2019 | Bar-Zeev et al. |
| 10,398,514 B2 | 9/2019 | Ryan et al. |
| 10,401,657 B2 | 9/2019 | Jiang et al. |
| 10,405,825 B2 | 9/2019 | Rai et al. |
| 10,405,927 B1 | 9/2019 | Lang |
| 10,413,752 B2 | 9/2019 | Berlinger et al. |
| 10,419,655 B2 | 9/2019 | Sivan |
| 10,420,626 B2 | 9/2019 | Tokuda et al. |
| 10,420,813 B2 | 9/2019 | Newell-Rogers et al. |
| 10,424,115 B2 | 9/2019 | Ellerbrock |
| D862,469 S | 10/2019 | Sadot et al. |
| 10,426,554 B2 | 10/2019 | Siewerdsen et al. |
| 10,429,675 B2 | 10/2019 | Greget |
| 10,431,008 B2 | 10/2019 | Djajadiningrat et al. |
| 10,433,814 B2 | 10/2019 | Razzaque et al. |
| 10,434,335 B2 | 10/2019 | Takahashi et al. |
| 10,441,236 B2 | 10/2019 | Bar-Tal et al. |
| 10,444,514 B2 | 10/2019 | Abou Shousha et al. |
| 10,447,947 B2 | 10/2019 | Liu |
| 10,448,003 B2 | 10/2019 | Grafenberg |
| 10,449,040 B2 | 10/2019 | Lashinski et al. |
| 10,453,187 B2 | 10/2019 | Peterson et al. |
| 10,463,434 B2 | 11/2019 | Siegler et al. |
| 10,465,892 B1 | 11/2019 | Feinbloom et al. |
| 10,466,487 B2 | 11/2019 | Blum et al. |
| 10,470,732 B2 | 11/2019 | Baumgart et al. |
| 10,473,314 B1 | 11/2019 | Braganca et al. |
| 10,485,989 B2 | 11/2019 | Jordan et al. |
| 10,488,663 B2 | 11/2019 | Choi |
| D869,772 S | 12/2019 | Gand |
| D870,977 S | 12/2019 | Berggren et al. |
| 10,492,755 B2 | 12/2019 | Lin et al. |
| 10,499,997 B2 | 12/2019 | Weinstein et al. |
| 10,502,363 B2 | 12/2019 | Edwards et al. |
| 10,504,231 B2 | 12/2019 | Fiala |
| 10,507,066 B2 | 12/2019 | Dimaio et al. |
| 10,511,822 B2 | 12/2019 | Casas |
| 10,517,544 B2 | 12/2019 | Taguchi et al. |
| 10,537,395 B2 | 1/2020 | Perez |
| 10,540,780 B1 | 1/2020 | Cousins et al. |
| 10,543,485 B2 | 1/2020 | Ismagilov et al. |
| 10,546,423 B2 | 1/2020 | Jones et al. |
| 10,548,557 B2 | 2/2020 | Lim et al. |
| 10,555,775 B2 | 2/2020 | Hoffman et al. |
| 10,568,535 B2 | 2/2020 | Roberts et al. |
| 10,571,696 B2 | 2/2020 | Urey et al. |
| 10,571,716 B2 | 2/2020 | Chapiro |
| 10,573,086 B2 | 2/2020 | Bar-Zeev et al. |
| 10,573,087 B2 | 2/2020 | Gallop et al. |
| 10,577,630 B2 | 3/2020 | Zhang et al. |
| 10,586,400 B2 | 3/2020 | Douglas |
| 10,591,737 B2 | 3/2020 | Yildiz et al. |
| 10,592,748 B1 | 3/2020 | Cousins et al. |
| 10,594,998 B1 | 3/2020 | Casas |
| 10,595,716 B2 | 3/2020 | Nazareth et al. |
| 10,601,950 B2 | 3/2020 | Devam et al. |
| 10,602,114 B2 | 3/2020 | Casas |
| 10,603,113 B2 | 3/2020 | Lang |
| 10,603,133 B2 | 3/2020 | Wang et al. |
| 10,606,085 B2 | 3/2020 | Toyama |
| 10,610,172 B2 | 4/2020 | Hummel et al. |
| 10,610,179 B2 | 4/2020 | Altmann |
| 10,613,352 B2 | 4/2020 | Knoll |
| 10,617,566 B2 | 4/2020 | Esmonde |
| 10,620,460 B2 | 4/2020 | Carabin |
| 10,621,738 B2 | 4/2020 | Miao et al. |
| 10,625,099 B2 | 4/2020 | Takahashi et al. |
| 10,626,473 B2 | 4/2020 | Mariani et al. |
| 10,631,905 B2 | 4/2020 | Asfora et al. |
| 10,631,907 B2 | 4/2020 | Zucker et al. |
| 10,634,331 B1 | 4/2020 | Feinbloom et al. |
| 10,634,921 B2 | 4/2020 | Blum et al. |
| 10,638,080 B2 | 4/2020 | Ovchinnikov et al. |
| 10,646,285 B2 | 5/2020 | Siemionow et al. |

(56) References Cited

U.S. PATENT DOCUMENTS

| | | | |
|---|---|---|---|
| 10,650,513 | B2 | 5/2020 | Penney et al. |
| 10,650,594 | B2 | 5/2020 | Jones et al. |
| 10,652,525 | B2 | 5/2020 | Woods |
| 10,653,495 | B2 | 5/2020 | Gregerson et al. |
| 10,660,715 | B2 | 5/2020 | Dozeman |
| 10,663,738 | B2 | 5/2020 | Carlvik et al. |
| 10,665,033 | B2 | 5/2020 | Bar-Zeev et al. |
| 10,670,937 | B2 | 6/2020 | Alton et al. |
| 10,672,145 | B2 | 6/2020 | Albiol et al. |
| 10,682,112 | B2 | 6/2020 | Pizaine et al. |
| 10,682,767 | B2 | 6/2020 | Grafenberg et al. |
| 10,687,901 | B2 | 6/2020 | Thomas |
| 10,691,397 | B1 | 6/2020 | Clements |
| 10,702,713 | B2 | 7/2020 | Mori et al. |
| 10,706,540 | B2 | 7/2020 | Merlet |
| 10,709,398 | B2 | 7/2020 | Schweizer |
| 10,713,801 | B2 | 7/2020 | Jordan et al. |
| 10,716,643 | B2 | 7/2020 | Justin et al. |
| 10,722,733 | B2 | 7/2020 | Takahashi |
| 10,725,535 | B2 | 7/2020 | Yu |
| 10,731,832 | B2 | 8/2020 | Koo |
| 10,732,721 | B1 | 8/2020 | Clements |
| 10,742,949 | B2 | 8/2020 | Casas |
| 10,743,939 | B1 | 8/2020 | Lang |
| 10,743,943 | B2 | 8/2020 | Razeto et al. |
| 10,747,315 | B2 | 8/2020 | Tungare et al. |
| 10,748,319 | B1 | 8/2020 | Tao et al. |
| 10,758,315 | B2 | 9/2020 | Johnson et al. |
| 10,777,094 | B1 | 9/2020 | Rao et al. |
| 10,777,315 | B2 | 9/2020 | Zehavi et al. |
| 10,781,482 | B2 | 9/2020 | Gubatayao et al. |
| 10,792,110 | B2 | 10/2020 | Leung et al. |
| 10,799,145 | B2 | 10/2020 | West et al. |
| 10,799,296 | B2 | 10/2020 | Lang |
| 10,799,298 | B2 | 10/2020 | Crawford et al. |
| 10,799,316 | B2 | 10/2020 | Sela et al. |
| 10,810,799 | B2 | 10/2020 | Tepper et al. |
| 10,818,019 | B2 | 10/2020 | Piat et al. |
| 10,818,101 | B2 | 10/2020 | Gallop et al. |
| 10,818,199 | B2 | 10/2020 | Buras et al. |
| 10,825,563 | B2 | 11/2020 | Gibby et al. |
| 10,827,164 | B2 | 11/2020 | Perreault et al. |
| 10,831,943 | B2 | 11/2020 | Santarone et al. |
| 10,835,296 | B2 | 11/2020 | Elimelech et al. |
| 10,838,206 | B2 | 11/2020 | Fortin-Deschnes et al. |
| 10,839,629 | B2 | 11/2020 | Jones et al. |
| 10,839,956 | B2 | 11/2020 | Beydoun et al. |
| 10,841,556 | B2 | 11/2020 | Casas |
| 10,842,002 | B2 | 11/2020 | Chang |
| 10,842,461 | B2 | 11/2020 | Johnson et al. |
| 10,849,691 | B2 | 12/2020 | Zucker et al. |
| 10,849,693 | B2 | 12/2020 | Lang |
| 10,849,710 | B2 | 12/2020 | Liu |
| 10,861,236 | B2 | 12/2020 | Geri et al. |
| 10,865,220 | B2 | 12/2020 | Ebetino et al. |
| 10,869,517 | B1 | 12/2020 | Halpern |
| 10,869,727 | B2 | 12/2020 | Yanof et al. |
| 10,872,472 | B2 | 12/2020 | Watola et al. |
| 10,877,262 | B1 | 12/2020 | Luxembourg |
| 10,877,296 | B2 | 12/2020 | Lindsey et al. |
| 10,878,639 | B2 | 12/2020 | Douglas et al. |
| 10,893,260 | B2 | 1/2021 | Trail et al. |
| 10,895,742 | B2 | 1/2021 | Schneider et al. |
| 10,895,743 | B2 | 1/2021 | Dausmann |
| 10,895,906 | B2 | 1/2021 | West et al. |
| 10,898,151 | B2 | 1/2021 | Harding et al. |
| 10,908,420 | B2 | 2/2021 | Lee et al. |
| 10,921,595 | B2 | 2/2021 | Rakshit et al. |
| 10,921,613 | B2 | 2/2021 | Gupta et al. |
| 10,928,321 | B2 | 2/2021 | Rawle |
| 10,928,638 | B2 | 2/2021 | Ninan et al. |
| 10,929,670 | B1 | 2/2021 | Troy et al. |
| 10,935,815 | B1 | 3/2021 | Cesar |
| 10,935,816 | B2 | 3/2021 | Ban et al. |
| 10,936,537 | B2 | 3/2021 | Huston |
| 10,939,973 | B2 | 3/2021 | Dimaio et al. |
| 10,939,977 | B2 | 3/2021 | Messinger et al. |
| 10,941,933 | B2 | 3/2021 | Ferguson |
| 10,946,108 | B2 | 3/2021 | Zhang et al. |
| 10,950,338 | B2 | 3/2021 | Douglas |
| 10,951,872 | B2 | 3/2021 | Casas |
| 10,964,095 | B1 | 3/2021 | Douglas |
| 10,964,124 | B1 | 3/2021 | Douglas |
| 10,966,768 | B2 | 4/2021 | Poulos |
| 10,969,587 | B2 | 4/2021 | McDowall et al. |
| 10,993,754 | B2 | 5/2021 | Kuntz et al. |
| 11,000,335 | B2 | 5/2021 | Dorman |
| 11,002,994 | B2 | 5/2021 | Jiang et al. |
| 11,006,093 | B1 | 5/2021 | Hegyi |
| 11,013,550 | B2 | 5/2021 | Rioux et al. |
| 11,013,560 | B2 | 5/2021 | Lang |
| 11,013,562 | B2 | 5/2021 | Marti et al. |
| 11,013,573 | B2 | 5/2021 | Chang |
| 11,013,900 | B2 | 5/2021 | Malek et al. |
| 11,016,302 | B2 | 5/2021 | Freeman et al. |
| 11,019,988 | B2 | 6/2021 | Fiebel et al. |
| 11,027,027 | B2 | 6/2021 | Manning et al. |
| 11,029,147 | B2 | 6/2021 | Abovitz et al. |
| 11,030,809 | B2 | 6/2021 | Wang |
| 11,041,173 | B2 | 6/2021 | Zhang et al. |
| 11,045,663 | B2 | 6/2021 | Mori et al. |
| 11,049,293 | B2 | 6/2021 | Chae et al. |
| 11,049,476 | B2 | 6/2021 | Fuchs et al. |
| 11,050,990 | B2 | 6/2021 | Casas |
| 11,057,505 | B2 | 7/2021 | Dharmatilleke |
| 11,058,390 | B1 | 7/2021 | Douglas |
| 11,061,257 | B1 | 7/2021 | Hakim |
| 11,064,904 | B2 | 7/2021 | Kay et al. |
| 11,065,062 | B2 | 7/2021 | Frushour et al. |
| 11,067,387 | B2 | 7/2021 | Marell et al. |
| 11,071,497 | B2 | 7/2021 | Hallack et al. |
| 11,079,596 | B2 | 8/2021 | Arizona |
| 11,087,039 | B2 | 8/2021 | Duff et al. |
| 11,090,019 | B2 | 8/2021 | Siemionow et al. |
| 11,097,129 | B2 | 8/2021 | Sakata et al. |
| 11,099,376 | B1 | 8/2021 | Steier et al. |
| 11,103,320 | B2 | 8/2021 | Leboeuf et al. |
| D930,162 | S | 9/2021 | Cremer et al. |
| 11,109,762 | B1 | 9/2021 | Steier et al. |
| 11,112,611 | B1 | 9/2021 | Kessler et al. |
| 11,122,164 | B2 | 9/2021 | Gigante |
| 11,123,604 | B2 | 9/2021 | Fung |
| 11,129,562 | B2 | 9/2021 | Roberts et al. |
| 11,132,055 | B2 | 9/2021 | Jones et al. |
| 11,135,015 | B2 | 10/2021 | Crawford et al. |
| 11,135,016 | B2 | 10/2021 | Frielinghaus et al. |
| 11,137,610 | B1 | 10/2021 | Kessler et al. |
| 11,141,221 | B2 | 10/2021 | Hobeika et al. |
| 11,153,549 | B2 | 10/2021 | Casas |
| 11,153,555 | B1 | 10/2021 | Healy et al. |
| 11,163,176 | B2 | 11/2021 | Karafin et al. |
| 11,164,324 | B2 | 11/2021 | Liu et al. |
| 11,166,006 | B2 | 11/2021 | Hegyi |
| 11,169,380 | B2 | 11/2021 | Manly et al. |
| 11,172,990 | B2 | 11/2021 | Lang |
| 11,179,136 | B2 | 11/2021 | Kohli et al. |
| 11,180,557 | B2 | 11/2021 | Noelle |
| 11,181,747 | B1 | 11/2021 | Kessler et al. |
| 11,185,891 | B2 | 11/2021 | Cousins et al. |
| 11,187,907 | B2 | 11/2021 | Osterman et al. |
| 11,202,682 | B2 | 12/2021 | Staunton et al. |
| 11,207,150 | B2 | 12/2021 | Healy et al. |
| 11,217,028 | B2 | 1/2022 | Jones et al. |
| 11,224,483 | B2 | 1/2022 | Steinberg et al. |
| 11,224,763 | B2 | 1/2022 | Takahashi et al. |
| 11,227,417 | B2 | 1/2022 | Berlinger et al. |
| 11,231,787 | B2 | 1/2022 | Isaacs et al. |
| 11,243,404 | B2 | 2/2022 | McDowall et al. |
| 11,244,508 | B2 | 2/2022 | Kazanzides et al. |
| 11,253,216 | B2 | 2/2022 | Crawford et al. |
| 11,253,323 | B2 | 2/2022 | Hughes et al. |
| 11,257,190 | B2 | 2/2022 | Mao et al. |
| 11,257,241 | B2 | 2/2022 | Tao |
| 11,263,772 | B2 | 3/2022 | Siemionow et al. |

(56) References Cited

U.S. PATENT DOCUMENTS

| | | |
|---|---|---|
| 11,269,401 B2 | 3/2022 | West et al. |
| 11,272,151 B2 | 3/2022 | Casas |
| 11,278,359 B2 | 3/2022 | Siemionow et al. |
| 11,278,413 B1 | 3/2022 | Lang |
| 11,280,480 B2 | 3/2022 | Wilt et al. |
| 11,284,846 B2 | 3/2022 | Graumann et al. |
| 11,291,521 B2 | 4/2022 | Im |
| 11,294,167 B2 | 4/2022 | Ishimoda |
| 11,297,285 B2 | 4/2022 | Pierce |
| 11,300,252 B2 | 4/2022 | Nguyen |
| 11,300,790 B2 | 4/2022 | Cheng et al. |
| 11,304,621 B2 | 4/2022 | Merschon et al. |
| 11,304,759 B2 | 4/2022 | Kovtun et al. |
| 11,307,402 B2 | 4/2022 | Steier et al. |
| 11,308,663 B2 | 4/2022 | Alhrishy et al. |
| 11,311,341 B2 | 4/2022 | Lang |
| 11,317,973 B2 | 5/2022 | Calloway et al. |
| 11,337,763 B2 | 5/2022 | Choi |
| 11,348,257 B2 | 5/2022 | Lang |
| 11,350,072 B1 | 5/2022 | Quiles Casas |
| 11,350,965 B2 | 6/2022 | Yilmaz et al. |
| 11,351,006 B2 | 6/2022 | Aferzon et al. |
| 11,354,813 B2 | 6/2022 | Piat et al. |
| 11,360,315 B2 | 6/2022 | Tu et al. |
| 11,373,342 B2 | 6/2022 | Stafford et al. |
| 11,382,699 B2 | 7/2022 | Wassall et al. |
| 11,382,700 B2 | 7/2022 | Calloway et al. |
| 11,382,712 B2 | 7/2022 | Elimelech et al. |
| 11,382,713 B2 | 7/2022 | Healy et al. |
| 11,389,252 B2 | 7/2022 | Gera et al. |
| 11,393,229 B2 | 7/2022 | Zhou et al. |
| 11,399,895 B2 | 8/2022 | Soper et al. |
| 11,402,524 B2 | 8/2022 | Song et al. |
| 11,406,338 B2 | 8/2022 | Tolkowsky |
| 11,412,202 B2 | 8/2022 | Hegyi |
| 11,423,554 B2 | 8/2022 | Borsdorf et al. |
| 11,430,203 B2 | 8/2022 | Navab et al. |
| 11,432,828 B1 | 9/2022 | Lang |
| 11,432,931 B2 | 9/2022 | Lang |
| 11,443,428 B2 | 9/2022 | Petersen et al. |
| 11,443,431 B2 | 9/2022 | Flossmann et al. |
| 11,452,568 B2 | 9/2022 | Lang |
| 11,452,570 B2 | 9/2022 | Tolkowsky |
| 11,460,915 B2 | 10/2022 | Frielinghaus et al. |
| 11,461,936 B2 | 10/2022 | Freeman et al. |
| 11,461,983 B2 | 10/2022 | Jones et al. |
| 11,464,580 B2 | 10/2022 | Kemp et al. |
| 11,464,581 B2 | 10/2022 | Calloway |
| 11,475,625 B1 | 10/2022 | Douglas |
| 11,478,214 B2 | 10/2022 | Siewerdsen et al. |
| 11,483,532 B2 | 10/2022 | Quiles Casas |
| 11,488,021 B2 | 11/2022 | Sun et al. |
| 11,490,986 B2 | 11/2022 | Ben-Yishai |
| 11,510,750 B2 | 11/2022 | Dulin et al. |
| 11,513,358 B2 | 11/2022 | McDowall et al. |
| 11,527,002 B2 | 12/2022 | Govari |
| 11,528,393 B2 | 12/2022 | Garofolo et al. |
| 11,544,031 B2 | 1/2023 | Harviainen |
| 11,573,420 B2 | 2/2023 | Sarma et al. |
| 11,589,927 B2 | 2/2023 | Oezbek et al. |
| 11,627,924 B2 | 4/2023 | Alexandroni et al. |
| 11,644,675 B2 | 5/2023 | Manly et al. |
| 11,648,016 B2 | 5/2023 | Hathaway et al. |
| 11,651,499 B2 | 5/2023 | Wang et al. |
| 11,657,518 B2 | 5/2023 | Ketcha et al. |
| 11,666,458 B2 | 6/2023 | Kim et al. |
| 11,669,984 B2 | 6/2023 | Siewerdsen et al. |
| 11,686,947 B2 | 6/2023 | Loyola et al. |
| 11,699,236 B2 | 7/2023 | Avital et al. |
| 11,712,582 B2 | 8/2023 | Miyazaki et al. |
| 11,715,210 B2 | 8/2023 | Haslam et al. |
| 11,719,941 B2 | 8/2023 | Russell |
| 11,730,389 B2 | 8/2023 | Farshad et al. |
| 11,733,516 B2 | 8/2023 | Edwin et al. |
| 11,734,901 B2 | 8/2023 | Jones et al. |
| 11,744,657 B2 | 9/2023 | Leboeuf et al. |
| 11,750,794 B2 | 9/2023 | Benishti et al. |
| 11,766,296 B2 | 9/2023 | Wolf et al. |
| 11,798,178 B2 | 10/2023 | Merlet |
| 11,801,097 B2 | 10/2023 | Crawford et al. |
| 11,801,115 B2 | 10/2023 | Elimelech et al. |
| 11,808,943 B2 | 11/2023 | Robaina et al. |
| 11,815,683 B2 | 11/2023 | Sears et al. |
| 11,826,111 B2 | 11/2023 | Mahfouz |
| 11,832,886 B2 | 12/2023 | Dorman |
| 11,838,493 B2 | 12/2023 | Healy et al. |
| 11,839,433 B2 | 12/2023 | Schaewe et al. |
| 11,839,501 B2 | 12/2023 | Takahashi et al. |
| 11,864,934 B2 | 1/2024 | Junio et al. |
| 11,885,752 B2 | 1/2024 | St-Aubin et al. |
| 11,892,647 B2 | 2/2024 | Hung et al. |
| 11,896,445 B2 | 2/2024 | Gera et al. |
| 11,900,620 B2 | 2/2024 | Lalys et al. |
| 11,914,155 B2 | 2/2024 | Zhu et al. |
| 11,918,310 B1 | 3/2024 | Roh et al. |
| 11,922,631 B2 | 3/2024 | Haslam et al. |
| 11,941,814 B2 | 3/2024 | Crawford et al. |
| 11,944,508 B1 | 4/2024 | Cowin et al. |
| 11,948,265 B2 | 4/2024 | Gibby et al. |
| 11,950,968 B2 | 4/2024 | Wiggermann |
| 11,957,420 B2 | 4/2024 | Lang |
| 11,961,193 B2 | 4/2024 | Pelzl et al. |
| 11,963,723 B2 | 4/2024 | Vilsmeier et al. |
| 11,972,582 B2 | 4/2024 | Yan et al. |
| 11,974,819 B2 | 5/2024 | Finley et al. |
| 11,974,887 B2 | 5/2024 | Elimelech et al. |
| 11,977,232 B2 | 5/2024 | Wu et al. |
| 11,980,429 B2 | 5/2024 | Wolf et al. |
| 11,980,506 B2 | 5/2024 | Wolf et al. |
| 11,980,507 B2 | 5/2024 | Elimelech et al. |
| 11,980,508 B2 | 5/2024 | Elimelech et al. |
| 11,983,824 B2 | 5/2024 | Avisar et al. |
| 12,002,171 B2 | 6/2024 | Jones et al. |
| 12,010,285 B2 | 6/2024 | Quiles Casas |
| 12,014,497 B2 | 6/2024 | Hong et al. |
| 12,019,314 B1 | 6/2024 | Steines et al. |
| 12,026,897 B2 | 7/2024 | Frantz et al. |
| 12,033,322 B2 | 7/2024 | Laaksonen et al. |
| 12,044,856 B2 | 7/2024 | Gera et al. |
| 12,044,858 B2 | 7/2024 | Gera et al. |
| 12,053,247 B1 | 8/2024 | Chiou |
| 12,056,830 B2 | 8/2024 | Cvetko et al. |
| 12,059,281 B2 | 8/2024 | Weingarten et al. |
| 12,063,338 B2 | 8/2024 | Quiles Casas |
| 12,063,345 B2 | 8/2024 | Benishti et al. |
| 12,069,233 B2 | 8/2024 | Benishti et al. |
| 12,076,158 B2 | 9/2024 | Geiger et al. |
| 12,076,196 B2 | 9/2024 | Elimelech et al. |
| 12,079,385 B2 | 9/2024 | Ben-Yishai et al. |
| 12,112,483 B2 | 10/2024 | Grady et al. |
| 12,114,933 B2 | 10/2024 | Seo et al. |
| 12,115,028 B2 | 10/2024 | Dulin et al. |
| 12,127,800 B2 | 10/2024 | Qian et al. |
| 12,133,772 B2 | 11/2024 | Calloway et al. |
| 12,136,176 B2 | 11/2024 | Spaas et al. |
| 12,142,365 B2 | 11/2024 | Kaethner et al. |
| 12,150,821 B2 | 11/2024 | Gera et al. |
| 12,178,666 B2 | 12/2024 | Wolf et al. |
| 12,186,028 B2 | 1/2025 | Gera et al. |
| 2002/0082498 A1 | 6/2002 | Wendt et al. |
| 2003/0059097 A1 | 3/2003 | Abovitz et al. |
| 2003/0117393 A1 | 6/2003 | Sauer et al. |
| 2003/0130576 A1 | 7/2003 | Seeley et al. |
| 2003/0156144 A1 | 8/2003 | Morita |
| 2003/0210812 A1 | 11/2003 | Khamene et al. |
| 2003/0225329 A1 | 12/2003 | Rossner et al. |
| 2004/0019263 A1 | 1/2004 | Jutras et al. |
| 2004/0030237 A1 | 2/2004 | Lee et al. |
| 2004/0138556 A1 | 7/2004 | Cosman |
| 2004/0152955 A1 | 8/2004 | Mcginley et al. |
| 2004/0171930 A1 | 9/2004 | Grimm et al. |
| 2004/0238732 A1 | 12/2004 | State et al. |
| 2005/0017972 A1 | 1/2005 | Poole et al. |
| 2005/0024586 A1 | 2/2005 | Teiwes et al. |

(56) References Cited

U.S. PATENT DOCUMENTS

| | | |
|---|---|---|
| 2005/0119639 A1 | 6/2005 | McCombs et al. |
| 2005/0154296 A1 | 7/2005 | Lechner et al. |
| 2005/0203367 A1 | 9/2005 | Ahmed et al. |
| 2005/0203380 A1 | 9/2005 | Sauer et al. |
| 2005/0215879 A1 | 9/2005 | Chuanggui |
| 2005/0267358 A1 | 12/2005 | Tuma et al. |
| 2006/0072124 A1 | 4/2006 | Smetak et al. |
| 2006/0134198 A1 | 6/2006 | Tawa et al. |
| 2006/0147100 A1 | 7/2006 | Fitzpatrick |
| 2006/0176242 A1 | 8/2006 | Jaramaz et al. |
| 2007/0018975 A1 | 1/2007 | Chuanggui et al. |
| 2007/0058261 A1 | 3/2007 | Sugihara et al. |
| 2007/0100325 A1 | 5/2007 | Jutras et al. |
| 2007/0183041 A1 | 8/2007 | McCloy et al. |
| 2007/0233371 A1 | 10/2007 | Stoschek et al. |
| 2007/0273610 A1 | 11/2007 | Baillot |
| 2008/0002809 A1 | 1/2008 | Bodduluri |
| 2008/0007645 A1 | 1/2008 | McCutchen |
| 2008/0035266 A1 | 2/2008 | Danziger |
| 2008/0085033 A1 | 4/2008 | Haven et al. |
| 2008/0159612 A1 | 7/2008 | Fu et al. |
| 2008/0183065 A1 | 7/2008 | Goldbach |
| 2008/0221625 A1 | 9/2008 | Hufner et al. |
| 2008/0253527 A1 | 10/2008 | Boyden et al. |
| 2008/0262812 A1 | 10/2008 | Arata et al. |
| 2008/0287728 A1 | 11/2008 | Mostafavi et al. |
| 2009/0005961 A1 | 1/2009 | Grabowski et al. |
| 2009/0018437 A1 | 1/2009 | Cooke |
| 2009/0024127 A1 | 1/2009 | Lechner et al. |
| 2009/0036902 A1 | 2/2009 | Dimaio et al. |
| 2009/0062869 A1 | 3/2009 | Claverie et al. |
| 2009/0099445 A1 | 4/2009 | Burger |
| 2009/0123452 A1 | 5/2009 | Madison |
| 2009/0227847 A1 | 9/2009 | Tepper et al. |
| 2009/0285366 A1 | 11/2009 | Essenreiter et al. |
| 2009/0300540 A1 | 12/2009 | Russell |
| 2010/0076305 A1 | 3/2010 | Maier-Hein et al. |
| 2010/0094308 A1 | 4/2010 | Tatsumi et al. |
| 2010/0106010 A1 | 4/2010 | Rubner et al. |
| 2010/0114110 A1 | 5/2010 | Taft et al. |
| 2010/0138939 A1 | 6/2010 | Bentzon et al. |
| 2010/0149073 A1 | 6/2010 | Chaum et al. |
| 2010/0172567 A1 | 7/2010 | Prokoski |
| 2010/0210939 A1 | 8/2010 | Hartmann et al. |
| 2010/0266220 A1 | 10/2010 | Zagorchev et al. |
| 2010/0274124 A1 | 10/2010 | Jascob et al. |
| 2011/0004259 A1 | 1/2011 | Stallings et al. |
| 2011/0098553 A1 | 4/2011 | Robbins et al. |
| 2011/0105895 A1 | 5/2011 | Kornblau et al. |
| 2011/0125159 A1 | 5/2011 | Hanson et al. |
| 2011/0125160 A1 | 5/2011 | Bagga et al. |
| 2011/0216060 A1 | 9/2011 | Weising et al. |
| 2011/0245625 A1 | 10/2011 | Trovato et al. |
| 2011/0248064 A1 | 10/2011 | Marczyk |
| 2011/0254922 A1 | 10/2011 | Schaerer et al. |
| 2011/0306873 A1 | 12/2011 | Shenai et al. |
| 2012/0014608 A1 | 1/2012 | Watanabe |
| 2012/0068913 A1 | 3/2012 | Bar-Zeev et al. |
| 2012/0078236 A1 | 3/2012 | Schoepp |
| 2012/0109151 A1 | 5/2012 | Maier-Hein et al. |
| 2012/0143050 A1 | 6/2012 | Heigl |
| 2012/0155064 A1 | 6/2012 | Waters |
| 2012/0162452 A1 | 6/2012 | Liu |
| 2012/0182605 A1 | 7/2012 | Hall et al. |
| 2012/0201421 A1 | 8/2012 | Hartmann et al. |
| 2012/0216411 A1 | 8/2012 | Wevers et al. |
| 2012/0224260 A1 | 9/2012 | Healy et al. |
| 2012/0238609 A1 | 9/2012 | Srivastava et al. |
| 2012/0245645 A1 | 9/2012 | Hanson et al. |
| 2012/0289777 A1 | 11/2012 | Chopra et al. |
| 2012/0306850 A1 | 12/2012 | Balan et al. |
| 2012/0320100 A1 | 12/2012 | Machida et al. |
| 2013/0002928 A1 | 1/2013 | Imai |
| 2013/0009853 A1 | 1/2013 | Hesselink et al. |
| 2013/0038632 A1 | 2/2013 | Dillavou et al. |
| 2013/0050258 A1 | 2/2013 | Liu et al. |
| 2013/0050833 A1 | 2/2013 | Lewis et al. |
| 2013/0057581 A1 | 3/2013 | Meier |
| 2013/0079829 A1 | 3/2013 | Globerman et al. |
| 2013/0083009 A1 | 4/2013 | Geisner et al. |
| 2013/0106833 A1 | 5/2013 | Fun |
| 2013/0135734 A1 | 5/2013 | Shafer et al. |
| 2013/0135738 A1 | 5/2013 | Shafer et al. |
| 2013/0190602 A1 | 7/2013 | Liao et al. |
| 2013/0195338 A1 | 8/2013 | Xu et al. |
| 2013/0209953 A1 | 8/2013 | Arlinsky et al. |
| 2013/0212453 A1 | 8/2013 | Gudai et al. |
| 2013/0234914 A1 | 9/2013 | Fujimaki |
| 2013/0234935 A1 | 9/2013 | Griffith |
| 2013/0237811 A1 | 9/2013 | Mihailescu et al. |
| 2013/0245461 A1 | 9/2013 | Maier-Hein et al. |
| 2013/0249787 A1 | 9/2013 | Morimoto |
| 2013/0249945 A1 | 9/2013 | Kobayashi |
| 2013/0265623 A1 | 10/2013 | Sugiyama et al. |
| 2013/0267838 A1 | 10/2013 | Fronk et al. |
| 2013/0278631 A1 | 10/2013 | Border et al. |
| 2013/0278635 A1 | 10/2013 | Maggiore |
| 2013/0300637 A1 | 11/2013 | Smits et al. |
| 2013/0300760 A1 | 11/2013 | Sugano et al. |
| 2013/0342571 A1 | 12/2013 | Kinnebrew et al. |
| 2013/0345718 A1* | 12/2013 | Crawford ............... A61B 34/76 606/130 |
| 2014/0031668 A1 | 1/2014 | Mobasser et al. |
| 2014/0049629 A1 | 2/2014 | Siewerdsen et al. |
| 2014/0088402 A1 | 3/2014 | Xu |
| 2014/0088990 A1 | 3/2014 | Nawana et al. |
| 2014/0104505 A1 | 4/2014 | Koenig |
| 2014/0105912 A1 | 4/2014 | Noelle |
| 2014/0114173 A1 | 4/2014 | Bar-Tal et al. |
| 2014/0142426 A1 | 5/2014 | Razzaque et al. |
| 2014/0168261 A1 | 6/2014 | Margolis et al. |
| 2014/0176661 A1 | 6/2014 | Smurro et al. |
| 2014/0177023 A1 | 6/2014 | Gao et al. |
| 2014/0189508 A1 | 7/2014 | Granchi et al. |
| 2014/0198129 A1 | 7/2014 | Liu et al. |
| 2014/0218291 A1 | 8/2014 | Kirk |
| 2014/0240484 A1 | 8/2014 | Kodama et al. |
| 2014/0243614 A1 | 8/2014 | Rothberg et al. |
| 2014/0256429 A1 | 9/2014 | Kobayashi et al. |
| 2014/0266983 A1 | 9/2014 | Christensen |
| 2014/0268356 A1 | 9/2014 | Bolas et al. |
| 2014/0270505 A1 | 9/2014 | McCarthy |
| 2014/0275760 A1 | 9/2014 | Lee et al. |
| 2014/0285404 A1 | 9/2014 | Takano et al. |
| 2014/0285429 A1 | 9/2014 | Simmons |
| 2014/0288413 A1 | 9/2014 | Hwang et al. |
| 2014/0300632 A1 | 10/2014 | Laor |
| 2014/0300967 A1 | 10/2014 | Tilleman et al. |
| 2014/0301624 A1 | 10/2014 | Barckow et al. |
| 2014/0303491 A1 | 10/2014 | Shekhar et al. |
| 2014/0320399 A1 | 10/2014 | Kim et al. |
| 2014/0333899 A1 | 11/2014 | Smithwick |
| 2014/0336461 A1 | 11/2014 | Reiter et al. |
| 2014/0340286 A1 | 11/2014 | Machida et al. |
| 2014/0361956 A1 | 12/2014 | Mikhailov et al. |
| 2014/0371728 A1 | 12/2014 | Vaughn |
| 2015/0005772 A1 | 1/2015 | Anglin et al. |
| 2015/0018672 A1 | 1/2015 | Blumhofer et al. |
| 2015/0031985 A1 | 1/2015 | Reddy et al. |
| 2015/0043798 A1 | 2/2015 | Carrell et al. |
| 2015/0070347 A1 | 3/2015 | Hofmann et al. |
| 2015/0084990 A1 | 3/2015 | Laor |
| 2015/0150641 A1 | 6/2015 | Daon et al. |
| 2015/0182293 A1 | 7/2015 | Yang et al. |
| 2015/0192776 A1 | 7/2015 | Lee et al. |
| 2015/0209119 A1 | 7/2015 | Theodore et al. |
| 2015/0230893 A1* | 8/2015 | Huwais ............... A61B 17/1604 433/173 |
| 2015/0261922 A1 | 9/2015 | Nawana et al. |
| 2015/0277123 A1 | 10/2015 | Chaum et al. |
| 2015/0282735 A1 | 10/2015 | Rossner |
| 2015/0287188 A1 | 10/2015 | Gazit et al. |
| 2015/0287236 A1 | 10/2015 | Winne et al. |
| 2015/0297314 A1 | 10/2015 | Fowler et al. |

(56) References Cited

U.S. PATENT DOCUMENTS

| | | |
|---|---|---|
| 2015/0305828 A1 | 10/2015 | Park et al. |
| 2015/0310668 A1 | 10/2015 | Ellerbrock |
| 2015/0338652 A1 | 11/2015 | Lim et al. |
| 2015/0338653 A1 | 11/2015 | Subramaniam et al. |
| 2015/0350517 A1 | 12/2015 | Duret et al. |
| 2015/0351863 A1 | 12/2015 | Plassky et al. |
| 2015/0363978 A1 | 12/2015 | Maimone et al. |
| 2015/0366620 A1 | 12/2015 | Cameron et al. |
| 2016/0015878 A1 | 1/2016 | Graham et al. |
| 2016/0022287 A1 | 1/2016 | Nehls |
| 2016/0030131 A1 | 2/2016 | Yang et al. |
| 2016/0054571 A1 | 2/2016 | Tazbaz et al. |
| 2016/0086380 A1 | 3/2016 | Vayser et al. |
| 2016/0103318 A1 | 4/2016 | Du et al. |
| 2016/0125603 A1 | 5/2016 | Tanji |
| 2016/0133051 A1 | 5/2016 | Aonuma et al. |
| 2016/0143699 A1 | 5/2016 | Tanji |
| 2016/0153004 A1 | 6/2016 | Zhang et al. |
| 2016/0163045 A1 | 6/2016 | Penney et al. |
| 2016/0175064 A1 | 6/2016 | Steinle et al. |
| 2016/0178910 A1 | 6/2016 | Giudicelli et al. |
| 2016/0191887 A1 | 6/2016 | Casas |
| 2016/0223822 A1 | 8/2016 | Harrison et al. |
| 2016/0228033 A1 | 8/2016 | Rossner |
| 2016/0246059 A1 | 8/2016 | Halpin et al. |
| 2016/0249989 A1 | 9/2016 | Devam et al. |
| 2016/0256223 A1 | 9/2016 | Haimerl et al. |
| 2016/0275684 A1 | 9/2016 | Elenbaas et al. |
| 2016/0297315 A1* | 10/2016 | Gonzalez .............. B60L 53/665 |
| 2016/0302870 A1 | 10/2016 | Wilkinson et al. |
| 2016/0324580 A1 | 11/2016 | Esterberg |
| 2016/0324583 A1 | 11/2016 | Kheradpir et al. |
| 2016/0339337 A1 | 11/2016 | Ellsworth et al. |
| 2017/0014119 A1 | 1/2017 | Capote et al. |
| 2017/0024634 A1 | 1/2017 | Miao et al. |
| 2017/0027650 A1 | 2/2017 | Merck et al. |
| 2017/0031163 A1 | 2/2017 | Gao et al. |
| 2017/0031179 A1 | 2/2017 | Guillot et al. |
| 2017/0045742 A1 | 2/2017 | Greenhalgh et al. |
| 2017/0065364 A1 | 3/2017 | Schuh et al. |
| 2017/0068119 A1 | 3/2017 | Antaki et al. |
| 2017/0076501 A1 | 3/2017 | Jagga et al. |
| 2017/0086941 A1 | 3/2017 | Marti et al. |
| 2017/0112586 A1 | 4/2017 | Dhupar |
| 2017/0164919 A1 | 6/2017 | Lavallee et al. |
| 2017/0164920 A1 | 6/2017 | Lavallee et al. |
| 2017/0178375 A1 | 6/2017 | Benishti et al. |
| 2017/0220224 A1 | 8/2017 | Kodali et al. |
| 2017/0239015 A1 | 8/2017 | Sela et al. |
| 2017/0245944 A1 | 8/2017 | Crawford et al. |
| 2017/0251900 A1 | 9/2017 | Hansen et al. |
| 2017/0252109 A1 | 9/2017 | Yang et al. |
| 2017/0258526 A1 | 9/2017 | Lang |
| 2017/0281283 A1 | 10/2017 | Siegler et al. |
| 2017/0312032 A1 | 11/2017 | Amanatullah et al. |
| 2017/0322950 A1 | 11/2017 | Han et al. |
| 2017/0348055 A1 | 12/2017 | Salcedo et al. |
| 2017/0348061 A1 | 12/2017 | Joshi et al. |
| 2017/0366773 A1 | 12/2017 | Kiraly et al. |
| 2017/0367766 A1 | 12/2017 | Mahfouz |
| 2017/0367771 A1 | 12/2017 | Tako et al. |
| 2017/0372477 A1 | 12/2017 | Penney et al. |
| 2018/0003981 A1 | 1/2018 | Urey |
| 2018/0018791 A1 | 1/2018 | Guoyi |
| 2018/0021597 A1 | 1/2018 | Berlinger et al. |
| 2018/0028266 A1 | 2/2018 | Barnes et al. |
| 2018/0036884 A1 | 2/2018 | Chen et al. |
| 2018/0049622 A1 | 2/2018 | Ryan et al. |
| 2018/0055579 A1 | 3/2018 | Daon et al. |
| 2018/0071029 A1* | 3/2018 | Srimohanarajah ........................ A41D 13/1209 |
| 2018/0078316 A1 | 3/2018 | Schaewe et al. |
| 2018/0082480 A1 | 3/2018 | White et al. |
| 2018/0092667 A1 | 4/2018 | Heigl et al. |
| 2018/0092698 A1 | 4/2018 | Chopra et al. |
| 2018/0092699 A1 | 4/2018 | Finley |
| 2018/0116732 A1 | 5/2018 | Lin et al. |
| 2018/0116741 A1 | 5/2018 | Garcia et al. |
| 2018/0117150 A1 | 5/2018 | O'Dwyer et al. |
| 2018/0120106 A1 | 5/2018 | Sato |
| 2018/0133871 A1 | 5/2018 | Farmer |
| 2018/0153626 A1 | 6/2018 | Yang et al. |
| 2018/0182150 A1 | 6/2018 | Benishti et al. |
| 2018/0185100 A1 | 7/2018 | Weinstein et al. |
| 2018/0185113 A1 | 7/2018 | Gregerson et al. |
| 2018/0193097 A1 | 7/2018 | McLachlin et al. |
| 2018/0200002 A1 | 7/2018 | Kostrzewski et al. |
| 2018/0247128 A1 | 8/2018 | Alvi et al. |
| 2018/0262743 A1 | 9/2018 | Casas |
| 2018/0303558 A1 | 10/2018 | Thomas |
| 2018/0311011 A1 | 11/2018 | Van et al. |
| 2018/0317803 A1 | 11/2018 | Ben-Yishai et al. |
| 2018/0318035 A1 | 11/2018 | McLachlin et al. |
| 2018/0368898 A1 | 12/2018 | Divincenzo et al. |
| 2019/0000372 A1 | 1/2019 | Gullotti et al. |
| 2019/0000564 A1 | 1/2019 | Navab et al. |
| 2019/0015163 A1 | 1/2019 | Abhari et al. |
| 2019/0018235 A1 | 1/2019 | Ouderkirk et al. |
| 2019/0038362 A1 | 2/2019 | Nash et al. |
| 2019/0038365 A1 | 2/2019 | Soper et al. |
| 2019/0043238 A1 | 2/2019 | Benishti et al. |
| 2019/0043392 A1 | 2/2019 | Abele |
| 2019/0046272 A1 | 2/2019 | Zoabi et al. |
| 2019/0046276 A1 | 2/2019 | Inglese et al. |
| 2019/0053851 A1 | 2/2019 | Siemionow et al. |
| 2019/0069971 A1 | 3/2019 | Tripathi et al. |
| 2019/0080515 A1 | 3/2019 | Geri et al. |
| 2019/0105116 A1 | 4/2019 | Johnson et al. |
| 2019/0130792 A1 | 5/2019 | Rios et al. |
| 2019/0142519 A1 | 5/2019 | Siemionow et al. |
| 2019/0144443 A1 | 5/2019 | Jackson et al. |
| 2019/0175228 A1 | 6/2019 | Elimelech et al. |
| 2019/0192230 A1 | 6/2019 | Siemionow et al. |
| 2019/0200894 A1 | 7/2019 | Jung et al. |
| 2019/0201106 A1 | 7/2019 | Siemionow et al. |
| 2019/0205606 A1 | 7/2019 | Zhou et al. |
| 2019/0216537 A1 | 7/2019 | Eltorai et al. |
| 2019/0251692 A1 | 8/2019 | Schmidt-Richberg et al. |
| 2019/0251694 A1 | 8/2019 | Han et al. |
| 2019/0254753 A1 | 8/2019 | Johnson et al. |
| 2019/0273916 A1 | 9/2019 | Benishti et al. |
| 2019/0310481 A1 | 10/2019 | Blum et al. |
| 2019/0324365 A1 | 10/2019 | De et al. |
| 2019/0333480 A1 | 10/2019 | Lang |
| 2019/0369660 A1 | 12/2019 | Wen et al. |
| 2019/0369717 A1 | 12/2019 | Frielinghaus et al. |
| 2019/0378276 A1 | 12/2019 | Flossmann et al. |
| 2019/0387351 A1 | 12/2019 | Lyren et al. |
| 2020/0015895 A1 | 1/2020 | Frielinghaus et al. |
| 2020/0019364 A1 | 1/2020 | Pond |
| 2020/0020249 A1 | 1/2020 | Jarc et al. |
| 2020/0038112 A1 | 2/2020 | Amanatullah et al. |
| 2020/0043160 A1 | 2/2020 | Mizukura et al. |
| 2020/0078100 A1 | 3/2020 | Weinstein et al. |
| 2020/0085511 A1 | 3/2020 | Oezbek et al. |
| 2020/0088997 A1 | 3/2020 | Lee et al. |
| 2020/0100847 A1 | 4/2020 | Siegler et al. |
| 2020/0117025 A1 | 4/2020 | Sauer |
| 2020/0129058 A1 | 4/2020 | Li et al. |
| 2020/0129136 A1 | 4/2020 | Harding et al. |
| 2020/0129262 A1 | 4/2020 | Verard et al. |
| 2020/0129264 A1 | 4/2020 | Oativia et al. |
| 2020/0133029 A1 | 4/2020 | Yonezawa |
| 2020/0138518 A1 | 5/2020 | Lang |
| 2020/0138618 A1 | 5/2020 | Roszkowiak et al. |
| 2020/0143594 A1 | 5/2020 | Lal et al. |
| 2020/0146546 A1 | 5/2020 | Chene et al. |
| 2020/0151507 A1 | 5/2020 | Siemionow et al. |
| 2020/0156259 A1 | 5/2020 | Ruiz et al. |
| 2020/0159313 A1 | 5/2020 | Gibby et al. |
| 2020/0163723 A1 | 5/2020 | Wolf et al. |
| 2020/0163739 A1 | 5/2020 | Messinger et al. |
| 2020/0178916 A1 | 6/2020 | Lalys et al. |
| 2020/0184638 A1 | 6/2020 | Meglan et al. |

(56) References Cited

U.S. PATENT DOCUMENTS

| | | |
|---|---|---|
| 2020/0186786 A1 | 6/2020 | Gibby et al. |
| 2020/0188028 A1 | 6/2020 | Feiner et al. |
| 2020/0188034 A1 | 6/2020 | Lequette et al. |
| 2020/0201082 A1 | 6/2020 | Carabin |
| 2020/0229877 A1 | 7/2020 | Siemionow et al. |
| 2020/0237256 A1 | 7/2020 | Farshad et al. |
| 2020/0237459 A1 | 7/2020 | Racheli et al. |
| 2020/0237880 A1 | 7/2020 | Kent et al. |
| 2020/0242280 A1 | 7/2020 | Pavloff et al. |
| 2020/0246074 A1 | 8/2020 | Lang |
| 2020/0246081 A1 | 8/2020 | Johnson et al. |
| 2020/0264451 A1 | 8/2020 | Blum et al. |
| 2020/0265273 A1 | 8/2020 | Wei et al. |
| 2020/0275988 A1 | 9/2020 | Johnson et al. |
| 2020/0281554 A1 | 9/2020 | Trini et al. |
| 2020/0286222 A1 | 9/2020 | Essenreiter et al. |
| 2020/0288075 A1 | 9/2020 | Bonin et al. |
| 2020/0294233 A1 | 9/2020 | Merlet |
| 2020/0297427 A1 | 9/2020 | Cameron et al. |
| 2020/0305980 A1 | 10/2020 | Lang |
| 2020/0315734 A1 | 10/2020 | El Amm |
| 2020/0321099 A1 | 10/2020 | Holladay et al. |
| 2020/0323460 A1 | 10/2020 | Busza et al. |
| 2020/0323609 A1 | 10/2020 | Johnson et al. |
| 2020/0327721 A1 | 10/2020 | Siemionow et al. |
| 2020/0330179 A1 | 10/2020 | Ton |
| 2020/0337780 A1 | 10/2020 | Winkler et al. |
| 2020/0341283 A1 | 10/2020 | McCracken et al. |
| 2020/0352655 A1 | 11/2020 | Freese |
| 2020/0355927 A1 | 11/2020 | Marcellin-Dibon et al. |
| 2020/0360091 A1 | 11/2020 | Murray et al. |
| 2020/0375666 A1 | 12/2020 | Murphy |
| 2020/0377493 A1 | 12/2020 | Heiser et al. |
| 2020/0377956 A1 | 12/2020 | Vogelstein et al. |
| 2020/0388075 A1 | 12/2020 | Kazanzides et al. |
| 2020/0389425 A1 | 12/2020 | Bhatia et al. |
| 2020/0390502 A1 | 12/2020 | Holthuizen et al. |
| 2020/0390503 A1 | 12/2020 | Casas et al. |
| 2020/0402647 A1 | 12/2020 | Domracheva et al. |
| 2020/0409306 A1 | 12/2020 | Gelman et al. |
| 2020/0410687 A1 | 12/2020 | Siemionow et al. |
| 2020/0413031 A1 | 12/2020 | Khani et al. |
| 2021/0004956 A1 | 1/2021 | Book et al. |
| 2021/0009339 A1 | 1/2021 | Morrison et al. |
| 2021/0015560 A1 | 1/2021 | Boddington et al. |
| 2021/0015583 A1 | 1/2021 | Avisar et al. |
| 2021/0022599 A1 | 1/2021 | Freeman et al. |
| 2021/0022808 A1 | 1/2021 | Lang |
| 2021/0022811 A1 | 1/2021 | Mahfouz |
| 2021/0022828 A1 | 1/2021 | Elimelech et al. |
| 2021/0029804 A1 | 1/2021 | Chang |
| 2021/0030374 A1 | 2/2021 | Takahashi et al. |
| 2021/0030511 A1 | 2/2021 | Wolf et al. |
| 2021/0038339 A1 | 2/2021 | Yu et al. |
| 2021/0049825 A1 | 2/2021 | Wheelwright et al. |
| 2021/0052348 A1 | 2/2021 | Stifter et al. |
| 2021/0056687 A1 | 2/2021 | Hibbard et al. |
| 2021/0065911 A1 | 3/2021 | Goel et al. |
| 2021/0077195 A1 | 3/2021 | Saeidi et al. |
| 2021/0077210 A1 | 3/2021 | Itkowitz et al. |
| 2021/0080751 A1 | 3/2021 | Lindsey et al. |
| 2021/0090344 A1 | 3/2021 | Geri et al. |
| 2021/0093391 A1 | 4/2021 | Poltaretskyi et al. |
| 2021/0093392 A1 | 4/2021 | Poltaretskyi et al. |
| 2021/0093400 A1 | 4/2021 | Quaid et al. |
| 2021/0093417 A1 | 4/2021 | Liu |
| 2021/0104055 A1 | 4/2021 | Ni et al. |
| 2021/0107923 A1 | 4/2021 | Jackson et al. |
| 2021/0109349 A1 | 4/2021 | Schneider et al. |
| 2021/0109373 A1 | 4/2021 | Loo et al. |
| 2021/0110517 A1 | 4/2021 | Flohr et al. |
| 2021/0113269 A1 | 4/2021 | Mlsmeier et al. |
| 2021/0113293 A9 | 4/2021 | Silva et al. |
| 2021/0121238 A1 | 4/2021 | Palushi et al. |
| 2021/0137634 A1 | 5/2021 | Lang |
| 2021/0141887 A1 | 5/2021 | Kim et al. |
| 2021/0150702 A1 | 5/2021 | Claessen et al. |
| 2021/0157544 A1 | 5/2021 | Denton |
| 2021/0160472 A1 | 5/2021 | Casas |
| 2021/0161614 A1 | 6/2021 | Elimelech et al. |
| 2021/0162287 A1 | 6/2021 | Xing et al. |
| 2021/0165207 A1 | 6/2021 | Peyman |
| 2021/0169504 A1 | 6/2021 | Brown |
| 2021/0169578 A1 | 6/2021 | Calloway et al. |
| 2021/0169581 A1 | 6/2021 | Calloway et al. |
| 2021/0169605 A1 | 6/2021 | Calloway et al. |
| 2021/0186647 A1 | 6/2021 | Elimelech et al. |
| 2021/0196404 A1 | 7/2021 | Wang |
| 2021/0211640 A1 | 7/2021 | Bristol et al. |
| 2021/0223577 A1 | 7/2021 | Zhang et al. |
| 2021/0225006 A1 | 7/2021 | Grady et al. |
| 2021/0227791 A1 | 7/2021 | De et al. |
| 2021/0231301 A1 | 7/2021 | Hikmet et al. |
| 2021/0235061 A1 | 7/2021 | Hegyi |
| 2021/0248822 A1 | 8/2021 | Choi et al. |
| 2021/0274281 A1 | 9/2021 | Zhang et al. |
| 2021/0278675 A1 | 9/2021 | Klug et al. |
| 2021/0282887 A1 | 9/2021 | Wiggermann |
| 2021/0290046 A1 | 9/2021 | Nazareth et al. |
| 2021/0290336 A1 | 9/2021 | Wang |
| 2021/0290394 A1 | 9/2021 | Mahfouz |
| 2021/0295108 A1 | 9/2021 | Bar |
| 2021/0295512 A1 | 9/2021 | Knoplioch et al. |
| 2021/0298795 A1 | 9/2021 | Bowling et al. |
| 2021/0298835 A1 | 9/2021 | Wang |
| 2021/0306599 A1 | 9/2021 | Pierce |
| 2021/0311322 A1 | 10/2021 | Belanger et al. |
| 2021/0314502 A1 | 10/2021 | Liu |
| 2021/0315636 A1 | 10/2021 | Akbarian et al. |
| 2021/0315662 A1 | 10/2021 | Freeman et al. |
| 2021/0325684 A1 | 10/2021 | Ninan et al. |
| 2021/0332447 A1 | 10/2021 | Lubelski et al. |
| 2021/0333561 A1 | 10/2021 | Oh et al. |
| 2021/0341739 A1 | 11/2021 | Cakmakci et al. |
| 2021/0341740 A1 | 11/2021 | Cakmakci et al. |
| 2021/0346115 A1 | 11/2021 | Dulin et al. |
| 2021/0349677 A1 | 11/2021 | Baldev et al. |
| 2021/0364802 A1 | 11/2021 | Uchiyama et al. |
| 2021/0369226 A1 | 12/2021 | Siemionow et al. |
| 2021/0371413 A1 | 12/2021 | Thurston et al. |
| 2021/0373333 A1 | 12/2021 | Moon |
| 2021/0373344 A1 | 12/2021 | Loyola et al. |
| 2021/0378757 A1 | 12/2021 | Bay et al. |
| 2021/0382310 A1 | 12/2021 | Freeman et al. |
| 2021/0386482 A1 | 12/2021 | Gera et al. |
| 2021/0389590 A1 | 12/2021 | Freeman et al. |
| 2021/0400247 A1 | 12/2021 | Casas |
| 2021/0401533 A1 | 12/2021 | Im |
| 2021/0402255 A1 | 12/2021 | Fung |
| 2021/0405369 A1 | 12/2021 | King |
| 2022/0003992 A1 | 1/2022 | Ahn |
| 2022/0007006 A1 | 1/2022 | Healy et al. |
| 2022/0008135 A1 | 1/2022 | Frielinghaus et al. |
| 2022/0038675 A1 | 2/2022 | Hegyi |
| 2022/0039873 A1 | 2/2022 | Harris |
| 2022/0051484 A1 | 2/2022 | Jones et al. |
| 2022/0054199 A1 | 2/2022 | Sivaprakasam et al. |
| 2022/0061921 A1 | 3/2022 | Crawford et al. |
| 2022/0071712 A1 | 3/2022 | Wolf et al. |
| 2022/0079675 A1 | 3/2022 | Lang |
| 2022/0087746 A1 | 3/2022 | Lang |
| 2022/0113810 A1 | 4/2022 | Isaacs et al. |
| 2022/0117669 A1 | 4/2022 | Nikou et al. |
| 2022/0121041 A1 | 4/2022 | Hakim |
| 2022/0133484 A1 | 5/2022 | Lang |
| 2022/0142730 A1 | 5/2022 | Wolf et al. |
| 2022/0155861 A1 | 5/2022 | Myung et al. |
| 2022/0159227 A1 | 5/2022 | Quiles Casas |
| 2022/0179209 A1 | 6/2022 | Cherukuri |
| 2022/0192776 A1 | 6/2022 | Gibby et al. |
| 2022/0193453 A1 | 6/2022 | Miyazaki et al. |
| 2022/0201274 A1 | 6/2022 | Achilefu et al. |
| 2022/0245400 A1 | 8/2022 | Siemionow et al. |
| 2022/0245821 A1 | 8/2022 | Ouzounis |

(56) References Cited

U.S. PATENT DOCUMENTS

| | | |
|---|---|---|
| 2022/0257206 A1 | 8/2022 | Hartley et al. |
| 2022/0269077 A1 | 8/2022 | Adema et al. |
| 2022/0270263 A1 | 8/2022 | Junio |
| 2022/0287676 A1 | 9/2022 | Steines et al. |
| 2022/0292786 A1 | 9/2022 | Pelzl et al. |
| 2022/0295033 A1 | 9/2022 | Quiles Casas |
| 2022/0296315 A1 | 9/2022 | Sokhanvar et al. |
| 2022/0304768 A1 | 9/2022 | Elimelech et al. |
| 2022/0351385 A1 | 11/2022 | Finley et al. |
| 2022/0353487 A1 | 11/2022 | Hegyi |
| 2022/0358759 A1 | 11/2022 | Cork et al. |
| 2022/0370152 A1 | 11/2022 | Lavallee et al. |
| 2022/0387130 A1 | 12/2022 | Spaas et al. |
| 2022/0392085 A1 | 12/2022 | Finley et al. |
| 2022/0397750 A1 | 12/2022 | Zhou et al. |
| 2022/0398752 A1 | 12/2022 | Yoon et al. |
| 2022/0398755 A1 | 12/2022 | Herrmann |
| 2022/0405935 A1 | 12/2022 | Flossmann et al. |
| 2023/0004013 A1 | 1/2023 | McCracken et al. |
| 2023/0009793 A1 | 1/2023 | Gera et al. |
| 2023/0025480 A1 | 1/2023 | Kemp et al. |
| 2023/0027801 A1 | 1/2023 | Qian et al. |
| 2023/0032731 A1 | 2/2023 | Hörndler et al. |
| 2023/0034189 A1 | 2/2023 | Gera et al. |
| 2023/0050636 A1 | 2/2023 | Yanof et al. |
| 2023/0053120 A1 | 2/2023 | Jamali et al. |
| 2023/0073041 A1 | 3/2023 | Samadani et al. |
| 2023/0085387 A1 | 3/2023 | Jones et al. |
| 2023/0087783 A1 | 3/2023 | Dulin et al. |
| 2023/0100078 A1 | 3/2023 | Toporek et al. |
| 2023/0123621 A1 | 4/2023 | Joshi et al. |
| 2023/0126207 A1 | 4/2023 | Wang |
| 2023/0129056 A1 | 4/2023 | Hemingway et al. |
| 2023/0131515 A1 | 4/2023 | Oezbek et al. |
| 2023/0149083 A1 | 5/2023 | Lin et al. |
| 2023/0162493 A1 | 5/2023 | Worrell et al. |
| 2023/0165640 A1 | 6/2023 | Dulin et al. |
| 2023/0169659 A1 | 6/2023 | Chen et al. |
| 2023/0196582 A1 | 6/2023 | Grady et al. |
| 2023/0200917 A1 | 6/2023 | Calloway et al. |
| 2023/0236426 A1 | 7/2023 | Manly et al. |
| 2023/0236427 A1 | 7/2023 | Chen |
| 2023/0245784 A1 | 8/2023 | Crawford et al. |
| 2023/0260142 A1 | 8/2023 | Chatterjee et al. |
| 2023/0290037 A1 | 9/2023 | Tasse et al. |
| 2023/0295302 A1 | 9/2023 | Bhagavatheeswaran et al. |
| 2023/0306590 A1 | 9/2023 | Jazdzyk et al. |
| 2023/0316550 A1 | 10/2023 | Hiasa |
| 2023/0326011 A1 | 10/2023 | Cutforth et al. |
| 2023/0326027 A1 | 10/2023 | Wahrenberg |
| 2023/0329799 A1 | 10/2023 | Gera et al. |
| 2023/0329801 A1 | 10/2023 | Elimelech et al. |
| 2023/0334664 A1 | 10/2023 | Lu et al. |
| 2023/0335261 A1 | 10/2023 | Reicher et al. |
| 2023/0359043 A1 | 11/2023 | Russell |
| 2023/0363832 A1 | 11/2023 | Mosadegh et al. |
| 2023/0371984 A1 | 11/2023 | Leuthardt et al. |
| 2023/0372053 A1 | 11/2023 | Elimelech et al. |
| 2023/0372054 A1 | 11/2023 | Elimelech et al. |
| 2023/0377171 A1 | 11/2023 | Hasler et al. |
| 2023/0377175 A1 | 11/2023 | Seok |
| 2023/0379448 A1 | 11/2023 | Benishti et al. |
| 2023/0379449 A1 | 11/2023 | Benishti et al. |
| 2023/0386022 A1 | 11/2023 | Tan et al. |
| 2023/0386067 A1 | 11/2023 | De et al. |
| 2023/0386153 A1 | 11/2023 | Rybnikov et al. |
| 2023/0394791 A1 | 12/2023 | Wang et al. |
| 2023/0397349 A1 | 12/2023 | Capelli et al. |
| 2023/0397957 A1 | 12/2023 | Crawford et al. |
| 2023/0410445 A1 | 12/2023 | Elimelech et al. |
| 2023/0419496 A1 | 12/2023 | Wuelker et al. |
| 2023/0420114 A1 | 12/2023 | Scholler et al. |
| 2024/0008935 A1 | 1/2024 | Wolf et al. |
| 2024/0016549 A1 | 1/2024 | Johnson et al. |
| 2024/0016572 A1 | 1/2024 | Elimelech et al. |
| 2024/0020831 A1 | 1/2024 | Johnson et al. |
| 2024/0020840 A1 | 1/2024 | Johnson et al. |
| 2024/0020862 A1 | 1/2024 | Johnson et al. |
| 2024/0022704 A1 | 1/2024 | Benishti et al. |
| 2024/0023946 A1 | 1/2024 | Wolf et al. |
| 2024/0041530 A1 | 2/2024 | Lang |
| 2024/0041558 A1 | 2/2024 | Siewerdsen et al. |
| 2024/0045491 A1 | 2/2024 | Sourov |
| 2024/0058064 A1 | 2/2024 | Weiser et al. |
| 2024/0062387 A1 | 2/2024 | Frantz et al. |
| 2024/0103271 A1 | 3/2024 | Zare Seisan |
| 2024/0103282 A1 | 3/2024 | Law et al. |
| 2024/0111163 A1 | 4/2024 | Law et al. |
| 2024/0122560 A1 | 4/2024 | Junio et al. |
| 2024/0126087 A1 | 4/2024 | Gera et al. |
| 2024/0127559 A1 | 4/2024 | Rybnikov et al. |
| 2024/0127578 A1 | 4/2024 | Hiasa |
| 2024/0129451 A1 | 4/2024 | Healy et al. |
| 2024/0130826 A1 | 4/2024 | Elimelech et al. |
| 2024/0134206 A1 | 4/2024 | Gera et al. |
| 2024/0144497 A1 | 5/2024 | Cvetko et al. |
| 2024/0156532 A1 | 5/2024 | Weiman et al. |
| 2024/0177445 A1 | 5/2024 | Galeotti et al. |
| 2024/0177458 A1 | 5/2024 | Zhang et al. |
| 2024/0180634 A1 | 6/2024 | Mikus |
| 2024/0184119 A1 | 6/2024 | Lee et al. |
| 2024/0185509 A1 | 6/2024 | Kovler et al. |
| 2024/0202926 A1 | 6/2024 | Crawford et al. |
| 2024/0202927 A1 | 6/2024 | Haslam et al. |
| 2024/0212111 A1 | 6/2024 | Genghi et al. |
| 2024/0233131 A1 | 7/2024 | Westerhoff et al. |
| 2024/0245463 A1 | 7/2024 | Vilsmeier et al. |
| 2024/0245474 A1 | 7/2024 | Weiman et al. |
| 2024/0248530 A1 | 7/2024 | Gibby et al. |
| 2024/0252252 A1 | 8/2024 | Lang |
| 2024/0261036 A1 | 8/2024 | Finley et al. |
| 2024/0261058 A1 | 8/2024 | Gera et al. |
| 2024/0265645 A1 | 8/2024 | Papar |
| 2024/0266033 A1 | 8/2024 | Freeman et al. |
| 2024/0268922 A1 | 8/2024 | Calloway et al. |
| 2024/0273740 A1 | 8/2024 | Gibby et al. |
| 2024/0281979 A1 | 8/2024 | Schrempf et al. |
| 2024/0296527 A1 | 9/2024 | Nett et al. |
| 2024/0303832 A1 | 9/2024 | Chen et al. |
| 2024/0307101 A1 | 9/2024 | Gera et al. |
| 2024/0312012 A1 | 9/2024 | Li et al. |
| 2024/0341853 A1 | 10/2024 | Gibby et al. |
| 2024/0341861 A1 | 10/2024 | Wolf et al. |
| 2024/0341910 A1 | 10/2024 | Wolf et al. |
| 2024/0355098 A1 | 10/2024 | Liu et al. |
| 2024/0374314 A1 | 11/2024 | Frey et al. |
| 2024/0377640 A1 | 11/2024 | Asaban et al. |
| 2024/0378708 A1 | 11/2024 | Kim et al. |
| 2024/0382283 A1 | 11/2024 | Kuhnert et al. |
| 2024/0386572 A1 | 11/2024 | Barasofsky et al. |
| 2024/0386682 A1 | 11/2024 | Cvetko et al. |
| 2024/0394883 A1 | 11/2024 | Liao et al. |
| 2024/0394985 A1 | 11/2024 | Hanlon et al. |
| 2024/0404065 A1 | 12/2024 | Gibbons et al. |
| 2024/0404106 A1 | 12/2024 | Wu et al. |
| 2024/0420337 A1 | 12/2024 | Li et al. |
| 2024/0420592 A1 | 12/2024 | Stone et al. |
| 2024/0423724 A1 | 12/2024 | Wolf et al. |
| 2024/0423750 A1 | 12/2024 | Elimelech et al. |
| 2025/0020931 A1 | 1/2025 | Gera et al. |

FOREIGN PATENT DOCUMENTS

| | | |
|---|---|---|
| CN | 109199563 A | 1/2019 |
| CN | 111915696 A | 11/2020 |
| CN | 112489047 A | 3/2021 |
| DE | 202004011567 U1 | 11/2004 |
| DE | 102014008153 A1 | 10/2014 |
| EP | 2868277 A1 | 5/2015 |
| EP | 3076660 A1 | 10/2016 |
| EP | 3123970 A1 | 2/2017 |
| EP | 3306567 A1 | 4/2018 |
| EP | 3320874 A1 | 5/2018 |
| EP | 3206583 B1 | 9/2020 |

(56) References Cited

FOREIGN PATENT DOCUMENTS

| | | |
|---|---|---|
| EP | 2625845 B1 | 3/2021 |
| EP | 3913423 A1 | 11/2021 |
| EP | 4287120 A1 | 12/2023 |
| EP | 4375948 A1 | 5/2024 |
| EP | 4459543 A1 | 11/2024 |
| GB | 2507314 A | 4/2014 |
| IL | 262864 A | 3/2019 |
| KR | 10-2014-0120155 A | 10/2014 |
| WO | 2006/002559 A1 | 1/2006 |
| WO | 2007/051304 A1 | 5/2007 |
| WO | 2007/115826 A2 | 10/2007 |
| WO | 2008/103383 A1 | 8/2008 |
| WO | 2010/067267 A1 | 6/2010 |
| WO | 2010/074747 A1 | 7/2010 |
| WO | 2012/061537 A2 | 5/2012 |
| WO | 2012/101286 A1 | 8/2012 |
| WO | 2013/112554 A1 | 8/2013 |
| WO | 2014/014498 A1 | 1/2014 |
| WO | 2014/024188 A1 | 2/2014 |
| WO | 2014/037953 A2 | 3/2014 |
| WO | 2014/113455 A1 | 7/2014 |
| WO | 2014/125789 A1 | 8/2014 |
| WO | 2014/167563 A1 | 10/2014 |
| WO | 2014/174067 A1 | 10/2014 |
| WO | 2015/058816 A1 | 4/2015 |
| WO | 2015/061752 A1 | 4/2015 |
| WO | 2015/109145 A1 | 7/2015 |
| WO | 2016/151506 A1 | 9/2016 |
| WO | 2017/042171 A1 | 3/2017 |
| WO | 2018/052966 A1 | 3/2018 |
| WO | 2018/073452 A1 | 4/2018 |
| WO | 2018/200767 A1 | 11/2018 |
| WO | 2018/206086 A1 | 11/2018 |
| WO | 2019/083431 A1 | 5/2019 |
| WO | 2019/135209 A1 | 7/2019 |
| WO | 2019/161477 A1 | 8/2019 |
| WO | 2019/195926 A1 | 10/2019 |
| WO | 2019/210353 A1 | 11/2019 |
| WO | 2019/211741 A1 | 11/2019 |
| WO | 2020/109903 A1 | 6/2020 |
| WO | 2020/109904 A1 | 6/2020 |
| WO | 2021/017019 A1 | 2/2021 |
| WO | 2021/019369 A1 | 2/2021 |
| WO | 2021/021979 A2 | 2/2021 |
| WO | 2021/023574 A1 | 2/2021 |
| WO | 2021/046455 A1 | 3/2021 |
| WO | 2021/048158 A1 | 3/2021 |
| WO | 2021/061459 A1 | 4/2021 |
| WO | 2021/062375 A1 | 4/2021 |
| WO | 2021/073743 A1 | 4/2021 |
| WO | 2021/087439 A1 | 5/2021 |
| WO | 2021/091980 A1 | 5/2021 |
| WO | 2021/112918 A1 | 6/2021 |
| WO | 2021/130564 A1 | 7/2021 |
| WO | 2021/137752 A1 | 7/2021 |
| WO | 2021/141887 A1 | 7/2021 |
| WO | 2021/145584 A1 | 7/2021 |
| WO | 2021/154076 A1 | 8/2021 |
| WO | 2021/183318 A2 | 9/2021 |
| WO | 2021/188757 A1 | 9/2021 |
| WO | 2021/255627 A1 | 12/2021 |
| WO | 2021/257897 A1 | 12/2021 |
| WO | 2021/258078 A1 | 12/2021 |
| WO | 2022/009233 A1 | 1/2022 |
| WO | 2022/053923 A1 | 3/2022 |
| WO | 2022/079565 A1 | 4/2022 |
| WO | 2022/180624 A1 | 9/2022 |
| WO | 2023/003952 A1 | 1/2023 |
| WO | 2023/281395 A1 | 1/2023 |
| WO | 2023/007418 A1 | 2/2023 |
| WO | 2023/011924 A1 | 2/2023 |
| WO | 2023/021448 A1 | 2/2023 |
| WO | 2023/021450 A1 | 2/2023 |
| WO | 2023/021451 A1 | 2/2023 |
| WO | 2023/026229 A1 | 3/2023 |
| WO | 2023/047355 A1 | 3/2023 |
| WO | 2023/072887 A1 | 5/2023 |
| WO | 2023/088986 A1 | 5/2023 |
| WO | 2023/158878 A1 | 8/2023 |
| WO | 2023/159104 A2 | 8/2023 |
| WO | 2023/161848 A1 | 8/2023 |
| WO | 2023/163933 A1 | 8/2023 |
| WO | 2023/175244 A1 | 9/2023 |
| WO | 2023/186996 A1 | 10/2023 |
| WO | 2023/202909 A1 | 10/2023 |
| WO | 2023/205212 A1 | 10/2023 |
| WO | 2023/205896 A1 | 11/2023 |
| WO | 2023/209014 A1 | 11/2023 |
| WO | 2023/229415 A1 | 11/2023 |
| WO | 2023/232492 A1 | 12/2023 |
| WO | 2023/240912 A1 | 12/2023 |
| WO | 2024/001140 A1 | 1/2024 |
| WO | 2024/002620 A1 | 1/2024 |
| WO | 2024/013642 A2 | 1/2024 |
| WO | 2024/018368 A2 | 1/2024 |
| WO | 2024/046760 A1 | 3/2024 |
| WO | 2024/052136 A1 | 3/2024 |
| WO | 2024/077077 A1 | 4/2024 |
| WO | 2024/121060 A1 | 6/2024 |
| WO | 2024/132609 A1 | 6/2024 |
| WO | 2024/145341 A1 | 7/2024 |
| WO | 2024/160896 A1 | 8/2024 |
| WO | 2024/165508 A1 | 8/2024 |
| WO | 2024/173251 A1 | 8/2024 |
| WO | 2024/186811 A1 | 9/2024 |
| WO | 2024/226797 A1 | 10/2024 |
| WO | 2024/251344 A1 | 12/2024 |

OTHER PUBLICATIONS

Everysight, Installing your RX Adaptor, accessed Mar. 13, 2024 at https://support.everysight.com/hc/en-us/articles/115000984571-Installing-your-RX-Adaptor.

Everysight, Raptor User Manual, copyright 2017, in 46 pages.

Frames Direct, InSpatialRx Prescription Insert, Prescription Insert for Magic Leap 1, accessed Mar. 8, 2024 at https://www.framesdirect.com/inspatialrx-prescription-insert.html.

International Search Report and Written Opinion received for PCT Patent Application No. PCT/IB2019/053524, mailed on Aug. 14, 2019, 9 pages.

Reddit, Notice on Prescription Lenses for Nreal Glasses, accessed Mar. 13, 2024 at https://www.reddit.com/r/nreal/comments/x1fte5/notice_on_prescription_lenses_for_nreal_glasses/.

Vuzix Blades, Prescription Lens Installation Guide, copyright 2020.

U.S. Appl. No. 18/365,643, filed Aug. 4, 2023, Head-Mounted Augmented Reality Near Eye Display Device.

U.S. Appl. No. 18/365,650, filed Aug. 4, 2023, SYSTEMS FOR FACILITATING AUGMENTED REALITY-ASSISTED MEDICAL PROCEDURES.

U.S. Appl. No. 17/585,629, filed Jan. 27, 2022, Fiducial Marker.

U.S. Appl. No. 18/400,739, filed Dec. 29, 2023, Mirroring in Image Guided Surgery.

U.S. Appl. No. 18/008,980, filed Dec. 8, 2022, Rotating Marker.

U.S. Appl. No. 17/388,064, filed Jul. 29, 2021, Rotating Marker and Adapter for Image-Guided Surgery.

U.S. Appl. No. 18/365,556, filed Aug. 4, 2023, Systems for Medical Image Visualization.

U.S. Appl. No. 18/398,837, filed Dec. 28, 2023, Adjustable Augmented Reality Eyewear for Image-Guided Medical Intervention.

U.S. Appl. No. 18/399,433, filed Dec. 28, 2023, Configurable Augmented Reality Eyewear for Image-Guided Medical Intervention.

U.S. Appl. No. 15/896,102 U.S. Pat. No. 10,134,166, filed Feb. 14, 2018 Nov. 20, 2018, Combining Video-Based and Optic-Based Augmented Reality in a Near Eye Display.

U.S. Appl. No. 16/159,740 U.S. Pat. No. 10,382,748, filed Oct. 15, 2018 Aug. 13, 2019, Combining Video-Based and Optic-Based Augmented Reality in a Near Eye Display.

(56) References Cited

OTHER PUBLICATIONS

U.S. Appl. No. 16/419,023 U.S. Pat. No. 11,750,794, filed May 22, 2019 Sep. 5, 2023, Combining Video-Based and Optic-Based Augmented Reality in a Near Eye Display.
U.S. Appl. No. 18/352,158, filed Jul. 13, 2023, Combining Video-Based and Optic-Based Augmented Reality in a Near Eye Display.
U.S. Appl. No. 18/365,643 U.S. Pat. No. 12,069,233, filed Aug. 4, 2023 Aug. 20, 2024, Head-Mounted Augmented Reality Near Eye Display Device.
U.S. Appl. No. 18/365,650 U.S. Pat. No. 12,063,345, filed Aug. 4, 2023 Aug. 13, 2024, Systems for Facilitating Augmented Reality-Assisted Medical Procedures.
U.S. Appl. No. 18/970,608, filed Dec. 5, 2024, Combining Video-Based and Optic-Based Augmented Reality in a Near Eye Display.
U.S. Appl. No. 19/028,204, filed Jan. 17, 2025, Combining Video-Based and Optic-Based Augmented Reality in a Near Eye Display.
U.S. Appl. No. 15/127,423 U.S. Pat. No. 9,928,629, filed Sep. 20, 2016 Mar. 27, 2018, Combining Video-Based and Optic-Based Augmented Reality in a Near Eye Display.
U.S. Appl. No. 16/120,480 U.S. Pat. No. 10,835,296, filed Sep. 4, 2018 Nov. 17, 2020, Spinous Process Clamp.
U.S. Appl. No. 17/067,831, filed Oct. 12, 2020, Spinous Process Clamp.
U.S. Appl. No. 18/030,072, filed Apr. 4, 2023, Spinous Process Clamp.
U.S. Appl. No. 18/365,590 U.S. Pat. No. 11,980,508, filed Aug. 4, 2023 May 14, 2024, Registration of a Fiducial Marker for an Augmented Reality System.
U.S. Appl. No. 18/365,571 U.S. Pat. No. 11,974,887, filed Aug. 4, 2023 May 7, 2024, Registration Marker for an Augmented Reality System.
U.S. Appl. No. 18/632,588, filed Apr. 11, 2024, Registration of a Fiducial Marker for an Augmented Reality System.
U.S. Appl. No. 17/045,766 U.S. Pat. No. 11,980,507, filed Oct. 7, 2020 May 14, 2024, Registration of a Fiducial Marker for an Augmented Reality System.
U.S. Appl. No. 16/199,281 U.S. Pat. No. 10,939,977, filed Nov. 26, 2018 Mar. 9, 2021, Positioning Marker.
U.S. Appl. No. 16/524,258 U.S. Pat. No. 11,980,506, filed Jul. 29, 2019 May 14, 2024, Fiducial Marker.
U.S. Appl. No. 18/631,804, filed Apr. 10, 2024, Fiducial Marker.
U.S. Appl. No. 17/585,629 U.S. Pat. No. 12,178,666, filed Jan. 27, 2022 Dec. 31, 2024, Fiducial Marker.
U.S. Appl. No. 18/949,164, filed Nov. 15, 2024, Fiducial Marker.
U.S. Appl. No. 16/724,297 U.S. Pat. No. 11,382,712, filed Dec. 22, 2019 Jul. 12, 2022, Mirroring in Image Guided Surgery.
U.S. Appl. No. 17/827,710 U.S. Pat. No. 11,801,115, filed May 29, 2022 Oct. 31, 2023, Mirroring in Image Guided Surgery.
U.S. Appl. No. 18/352,181, filed Jul. 13, 2023, Mirroring in Image Guided Surgery.
U.S. Appl. No. 18/400,739 U.S. Pat. No. 12,076,196, filed Dec. 29, 2023 Sep. 3, 2024, Mirroring in Image Guided Surgery.
U.S. Appl. No. 18/780,095, filed Jul. 22, 2024, Mirroring in Image Guided Surgery.
U.S. Appl. No. 16/200,144 U.S. Pat. No. 11,766,296, filed Nov. 26, 2018 Sep. 26, 2023, Tracking System for Image-Guided Surgery.
U.S. Appl. No. 18/470,809 U.S. Pat. No. 11,980,429, filed Sep. 20, 2023 May 14, 2024, Tracking Methods for Image-Guided Surgery.
U.S. Appl. No. 18/631,877, filed Apr. 10, 2024, Tracking Systems and Methods for Image-Guided Surgery.
U.S. Appl. No. 18/978,615, filed Dec. 12, 2024, Tracking Systems and Methods for Image-Guided Surgery.
U.S. Appl. No. 19/027,864, filed Jan. 17, 2025, Tracking Systems and Methods for Image-Guided Surgery.
U.S. Appl. No. 17/015,199, filed Sep. 9, 2020, Universal Tool Adapter.
U.S. Appl. No. 18/598,965, filed Mar. 7, 2024, Universal Tool Adapter for Image Guided Surgery.
U.S. Appl. No. 18/044,380, filed Mar. 8, 2023, Universal Tool Adapter for Image-Guided Surgery.
U.S. Appl. No. 18/988,285, filed Dec. 19, 2024, Universal Tool Adapter.
U.S. Appl. No. 16/901,026 U.S. Pat. No. 11,389,252, filed Jun. 15, 2020 Jul. 19, 2022, Rotating Marker for Image Guided Surgery.
U.S. Appl. No. 18/008,980 U.S. Pat. No. 12,186,028, filed Dec. 8, 2022 Jan. 7, 2025, Rotating Marker.
U.S. Appl. No. 18/959,270, filed Nov. 25, 2024, Rotating Marker.
U.S. Appl. No. 17/368,859 U.S. Pat. No. 11,896,445, filed Jul. 7, 2021 Feb. 13, 2024, Iliac Pin and Adapter.
U.S. Appl. No. 18/437,898, filed Feb. 9, 2024, Iliac Pin and Adapter.
U.S. Appl. No. 18/576,516, filed Jan. 4, 2024, Iliac Pin and Adapter.
U.S. Appl. No. 17/388,064 U.S. Pat. No. 12,150,821, filed Jul. 29, 2021 Nov. 26, 2024, Rotating Marker and Adapter for Image-Guided Surgery.
U.S. Appl. No. 18/291,731, filed Jan. 24, 2024, Rotating Marker and Adapter for Image-Guided Surgery.
U.S. Appl. No. 18/930,558, filed Oct. 29, 2024, Rotating Marker and Adapter for Image-Guided Surgery.
U.S. Appl. No. 18/365,844, filed Aug. 4, 2023, Augmented-Reality Surgical System Using Depth Sensing.
U.S. Appl. No. 18/683,676, filed Feb. 14, 2024, Stereoscopic Display and Digital Loupe for Augmented-Reality Near-Eye Display.
U.S. Appl. No. 18/683,680, filed Feb. 14, 2024, Augmented Reality Assistance for Osteotomy and Discectomy.
U.S. Appl. No. 18/684,756, filed Feb. 19, 2024, Registration and Registration Validation in Image-Guided Surgery.
U.S. Appl. No. 18/693,338, filed Mar. 19, 2024, Surgical Planning and Display.
U.S. Appl. No. 18/365,566, filed Aug. 4, 2023, Systems for Medical Image Visualization.
U.S. Appl. No. 18/399,253, filed Dec. 28, 2023, Methods for Medical Image Visualization.
U.S. Appl. No. 18/857,558, filed Oct. 17, 2024, Reduction of Jitter in Virtual Presentation.
U.S. Appl. No. 18/995,731, filed Jan. 16, 2025, Calibration and Registration of Pre-Operative and Intraoperative Images.
U.S. Appl. No. 18/398,837 U.S. Pat. No. 12,044,858, filed Dec. 28, 2023 Jul. 23, 2024, Adjustable Augmented Reality Eyewear for Image-Guided Medical Intervention.
U.S. Appl. No. 18/399,433 U.S. Pat. No. 12,044,856, filed Dec. 28, 2023 Jul. 23, 2024, Configurable Augmented Reality Eyewear for Image-Guided Medical Intervention.
U.S. Appl. No. 18/772,578, filed Jul. 15, 2024, Augmented Reality Eyewear for Image-Guided Medical Intervention.
U.S. Appl. No. 35/508,942 D 930,162, filed Feb. 13, 2020 Sep. 7, 2021, Medical Headset.

\* cited by examiner

REGISTRATION OF A FIDUCIAL MARKER FOR AN AUGMENTED REALITY SYSTEM

CROSS-REFERENCE TO RELATED APPLICATIONS

This application is a continuation of U.S. application Ser. No. 17/045,766, filed on Oct. 7, 2020, now U.S. Pat. No. 11,980,507, which is a national stage entry of International PCT Application No. PCT/IB2019/053524, filed on Apr. 30, 2019, which claims the benefit of U.S. Provisional Patent Application 62/665,541, filed May 2, 2018, each of which is incorporated herein by reference in its entirety.

FIELD OF THE INVENTION

This invention relates generally to an augmented reality system, and specifically to accurate registration of different elements operating in the system when it is used for a medical procedure.

BACKGROUND OF THE INVENTION

For a medical professional to use an augmented reality system during a medical procedure, typically with a purpose built head mounted display, some images presented to the professional on the display may need to be aligned with the patient undergoing the procedure. Although some misalignment may be acceptable, for satisfactory presentation of the images the misalignment may typically not be more than about 2-3 mm. Ensuring such a limit on the misalignment requires accurate registration of the patient's anatomy with the presented images.

If the medical procedure involves surgery exposing internal elements of the patient, the registration typically involves registration of patient images determined in different modalities, in which case the misalignment should be typically 2 mm or less. For example, depending on the procedure being performed, internal patient elements such as bones may be imaged using a first modality comprising computerized tomography (CT) imaging, while the augmented reality system presents these elements optically, i.e., using a second modality.

However, the required registration may not be simple to achieve, because of limitations of the imaging systems. In the above example, the CT imaging modality may have a limited field of view, so that it is unable to simultaneously image a tracking patient marker (required for the optical augmented reality system) and patient bones such as the spine. An optical imaging modality is unable to simultaneously image the patient marker and the spine, since the latter is invisible.

U.S. Pat. No. 7,556,428, to Sukovic et al. describes a surgical navigation system that is claimed to overcome the problem of the narrow field of view of a CT scanner. A patient tracker, having locators, is positioned on the patient, typically on the patient's forehead, and a tracking system tracks the positions and orientations of the locators. Sukovic states that a "registration appendage" includes radio-opaque markers, and may be "removably secured to the patient tracker in a known position and orientation relative to the patient tracker". Sukovic further states that "When the locators of the patient tracker are positioned outside of the field of view of the CT scanner, the registration appendage can be secured to the patient tracker."

As is apparent from Sukovic's disclosure, the patient tracker and registration appendage relative positions must initially be known, and the two elements need to be physically secured together in order for Sukovic's system to function. Both of these requirements introduce limitations into the functioning of Sukovic's surgical navigation system.

Documents incorporated by reference in the present patent application are to be considered an integral part of the application except that, to the extent that any terms are defined in these incorporated documents in a manner that conflicts with definitions made explicitly or implicitly in the present specification, only the definitions in the present specification should be considered.

SUMMARY OF THE INVENTION

An embodiment of the present invention provides a registration marker, including:
 a radiotransparent substrate;
 a pattern formed in at least two dimensions, which is disposed on the substrate and is optically visible; and
 a multiplicity of radiopaque elements, which are disposed in the substrate and are spatially arranged in at least two dimensions to provide a unique pattern.

In a disclosed embodiment the optically visible pattern and/or said unique pattern have no axis of symmetry and no plane of symmetry.

In a further disclosed embodiment the radiotransparent substrate is optically opaque and includes a surface, and the pattern is fixedly mounted on the surface.

In a yet further disclosed embodiment the pattern includes optically reflective discrete elements fixedly mounted on the surface. The discrete elements may have a common size and shape, and locations of the discrete elements are selected to form the pattern.

The discrete elements may consist of a given discrete element and remaining discrete elements having a common size, wherein the given discrete element has a different size from the remaining discrete elements.

Alternatively or additionally the discrete elements may consist of a given discrete element and remaining discrete elements having a common shape, wherein the given discrete element has a different shape from the remaining discrete elements.

In an alternative embodiment the substrate includes a pillar attached to a rectangular parallelepiped, and the pattern includes optically reflective discrete elements, wherein one of the discrete elements is mounted on the pillar.

In a further alternative embodiment the substrate includes an indentation formed within a rectangular parallelepiped, and the pattern includes optically reflective discrete elements, wherein one of the discrete elements is mounted on a surface of the indentation.

The pattern may be formed in two dimensions. Alternatively the pattern may be formed in three dimensions.

The radiopaque elements may be spatially arranged in two dimensions. Alternatively the radiopaque elements may be spatially arranged in three dimensions.

The radiopaque elements may have a common size and shape, and locations of the radiopaque elements may be selected to form the unique pattern.

The radiopaque elements may consist of a given radiopaque element and remaining radiopaque elements having a common size, and the given radiopaque element may have a different size from the remaining radiopaque elements.

The radiopaque elements may consist of a given radiopaque element and remaining radiopaque elements having a common shape, and the given radiopaque element may have a different shape from the remaining radiopaque elements.

There is further provided, according to an embodiment of the present invention a method, including:

providing a radiotransparent substrate;

disposing a pattern formed in at least two dimensions and which is optically visible on the substrate; and disposing in the substrate a multiplicity of radiopaque elements, the elements being spatially arranged in at least two dimensions to provide a unique pattern.

There is further provided, according to an embodiment of the present invention, a method for registering a patient marker with a skeleton of a patient, including:

attaching the patient marker to a portion of the skeleton, the patient marker having a patient marker frame of reference;

providing a registration marker, including:

a radiotransparent substrate;

a pattern formed in at least two dimensions, which is disposed on the substrate and is optically visible, and which has no axis of symmetry and no plane of symmetry; and a multiplicity of radiopaque elements, which are disposed in the substrate and are spatially arranged in at least two dimensions to have no axis of symmetry and no plane of symmetry;

positioning the registration marker in proximity to the patient marker;

analyzing an optical image of the registration marker and the patient marker to determine a first relation between the patient marker frame of reference and a registration marker frame of reference;

analyzing a fluoroscopic image of the registration marker and the skeleton of the patient to determine a second relation between the registration marker frame of reference and the skeleton of the patient; and using the first and second relations to formulate a registration relation between the patient marker and the skeleton.

There is further provided, according to an embodiment of the present invention, apparatus, including:

a patient marker configured to be attached to a portion of a skeleton of a patient, the patient marker having a patient marker frame of reference;

a registration marker, including:

a radiotransparent substrate, a pattern formed in at least two dimensions, which is disposed on the substrate and is optically visible, and which has no axis of symmetry and no plane of symmetry, and a multiplicity of radiopaque elements, which are disposed in the substrate and are spatially arranged in at least two dimensions to have no axis of symmetry and no plane of symmetry; and a processor, configured to:

analyze an optical image of the patient marker and the registration marker, positioned in proximity to the patient marker, so as to determine a first relation between the patient marker frame of reference and a registration marker frame of reference, analyze a fluoroscopic image of the registration marker and the skeleton of the patient to determine a second relation between the registration marker frame of reference and the skeleton of the patient, and use the first and second relations to formulate a registration relation between the patient marker and the skeleton.

The present disclosure will be more fully understood from the following detailed description of the embodiments thereof, taken together with the drawings. A brief description of the drawings follows.

DETAILED DESCRIPTION OF EMBODIMENTS

Overview

Figure 1:
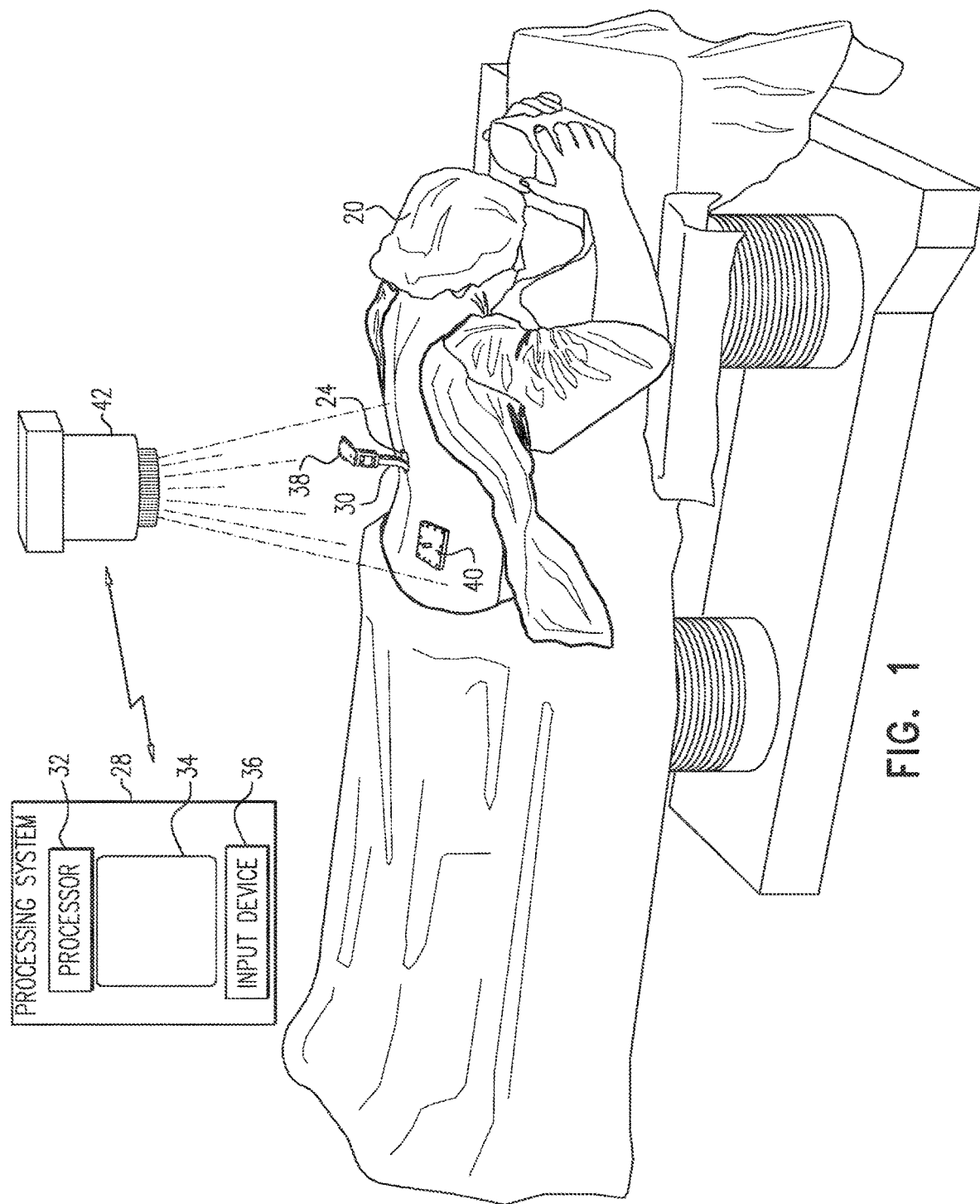
FIG. 1 is a schematic illustration of an initial preparatory stage of a medical procedure, according to an embodiment of the present invention.

Embodiments of the present invention overcome the problem of a narrow field of view of a fluoroscopic imaging system, such as a CT scanner, by using a patient marker and a registration marker, where the latter may be located in substantially any position relative to the former, and where the markers are not physically connected.

As described in more detail below, embodiments of the present invention provide a system for accurately registering a patient marker, visible in a first, optical, modality, that is attached to a spinous process of a patient, visible in a second, fluoroscopic, modality. The registration is performed during an initial stage of a procedure on the spine of the patient. In order to provide such accurate registration, embodiments of the invention use a registration marker which is configured to be visible in both modalities, i.e., both optically and under fluoroscopic imaging.

The registration marker comprises a radiotransparent substrate upon which a pattern, which is optically visible, is disposed. The pattern is configured to be in at least two dimensions, i.e., it may be formed in two dimensions or in three dimensions. Said pattern is unique and provides an unambiguous position and frame of reference of the registration marker. According to a preferred embodiment, said pattern is configured to have no axis of symmetry and no plane of symmetry. Alternatively, said unique pattern may be provided by optically reflective elements of different shapes and/or sizes so that an optical image of the pattern provides an unambiguous position and orientation of a frame of reference (FOR) of the registration marker.

The registration marker also comprises a multiplicity of radiopaque elements which are disposed in the substrate. The radiopaque elements are spatially arranged to be in at least two dimensions, i.e., the elements may be arranged to be in two dimensions or to be in three dimensions. As for the pattern described above, the pattern disposed by said radiopaque elements is unique and provides an unambiguous position and frame of reference of the registration marker. According to a preferred embodiment, the arrangement of the radiopaque elements also has no axis of symmetry and no plane of symmetry, so that a fluoroscopic image of the substrate provides the unambiguous position and orientation of the FOR of the registration marker. Alternatively, said unique pattern may be provided by radiopaque elements of different shapes and/or sizes.

In the initial stage of the procedure, the patient marker is clamped to a patient spinous process, and the registration marker is placed on the patient's back in proximity to the marker.

A fluoroscopic image of the registration marker and the patient's spine is acquired, and a first relation between a registration marker FOR and the spine is formulated from the image. For the fluoroscopic image acquisition, only the registration marker and the patient's spine are visible to the fluoroscope. As is explained further below, only the registration marker is subject to fluoroscopy. The patient marker is not subject to fluoroscopy.

In addition, a camera acquires an optical image of the patient marker and the registration marker, and a second relation between the registration marker FOR and the patient marker is formulated. For the optical image, only the registration marker and the patient marker are visible to the camera.

The two relations are then combined to provide an accurate relation registering the patient marker with the patient spine.

The relation found may be used by an augmented reality system operated in a medical procedure on the spine of the patient, for example by presenting vertebrae images that are accurately registered with the actual vertebrae.

DETAILED DESCRIPTION

In the following, all directional references (e.g., upper, lower, upward, downward, left, right, top, bottom, above, below, vertical, and horizontal) are only used for identification purposes to aid the reader's understanding of the present invention, and do not create limitations, particularly as to the position, orientation, or use of embodiments of the invention.

Figure 3:
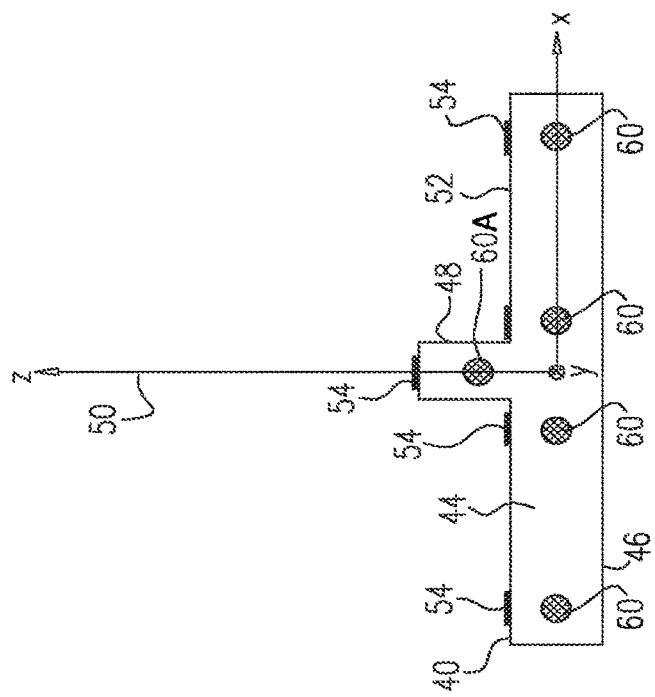
FIGS. 2, 3, and 4 are schematic depictions of entities used in the initial stage, according to an embodiment of the present invention.
Figure 2:
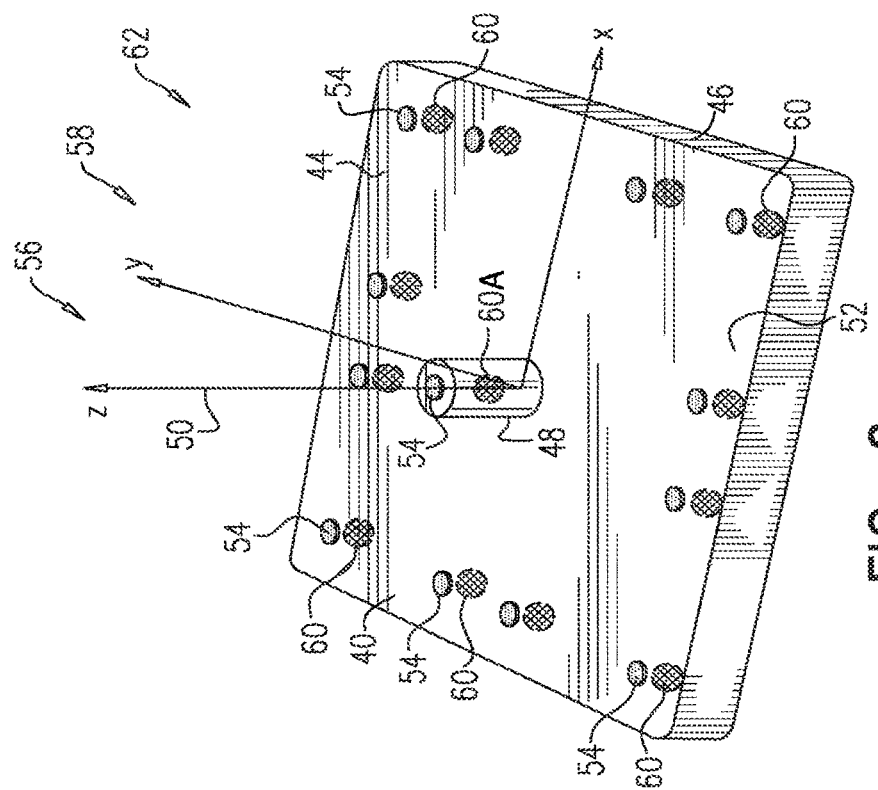
Figure 4:
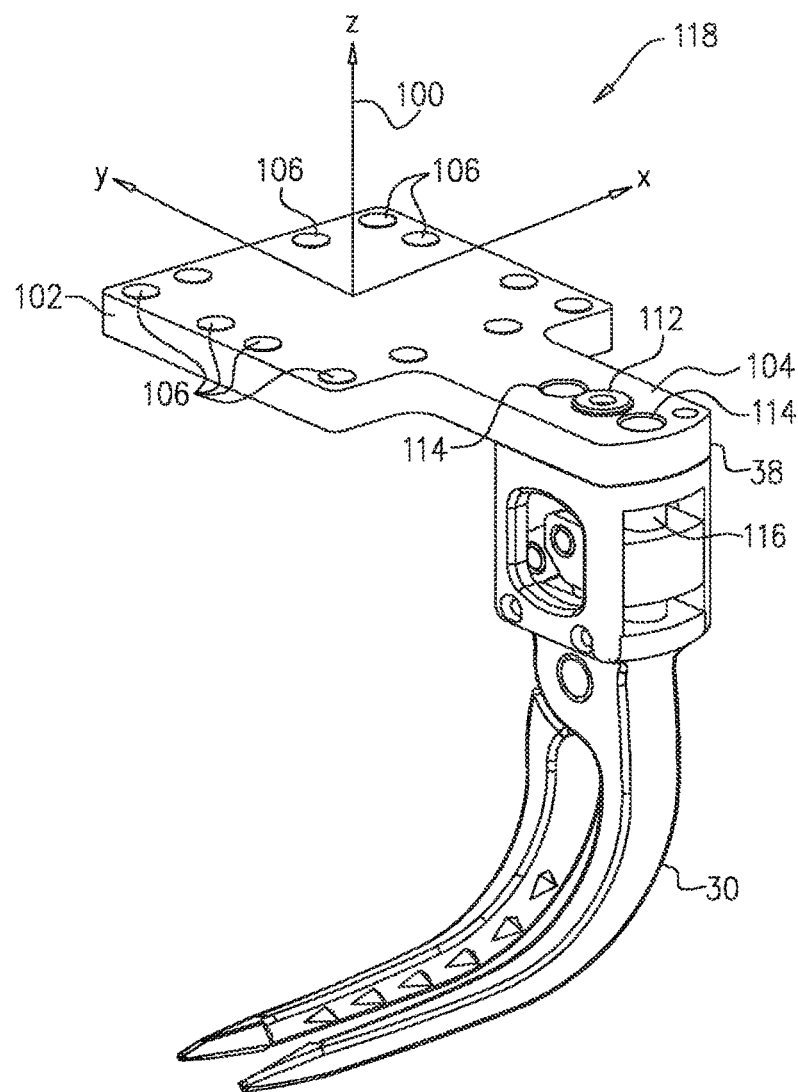

Reference is now made to FIGS. 1, 2, 3, and 4, which are diagrams according to an embodiment of the present invention. FIG. 1 is a schematic illustration of an initial preparatory stage of a medical procedure, and FIGS. 2, 3, and 4 are schematic depictions of entities used in the initial stage. The medical procedure exemplified here is performed on the back of a patient 20, and during the initial stage of the procedure a medical professional (not shown in FIG. 1) makes an incision 24 into the patient's back. The professional inserts a spinous process clamp 30 into the incision, so that opposing jaws of the clamp are located on opposite sides of the spinous processes. The professional then slides the clamp over the vertebral laminas, and adjusts the clamp to grip one or more spinous processes, selected by the professional, of the patient. Clamp 30 is described below with reference to FIG. 4, and a clamp such as clamp 30 is described in more detail in U.S. Provisional Patent Application 62/595,598 which is incorporated herein by reference.

Clamp 30 acts as a support for a patient marker 38, which is attached rigidly to the clamp. During substantially all of the procedure, i.e., during the initial, as well as the subsequent stages, patient marker 38 is used as a fiducial for patient 30, since because of its rigid connection to the patient, any movement of the patient is reflected in a corresponding motion of the patient marker. In order to operate as such a fiducial, in embodiments of the present invention, in the initial stage of the procedure marker 38 is registered with the anatomy of patient 30, herein assumed to comprise the skeleton of the patient, as is described herein.

During the initial stage of the procedure, a registration marker 40 is placed on the patient's back, and is used to implement the registration of patient marker 38 with the anatomy of patient 30. In contrast to patient marker 38, registration marker 40 is typically only used during the initial stage of the procedure, i.e., for the registration of the patient marker 38, and once the registration has been performed, for the subsequent procedure stages the registration marker may be removed from the patient's back. As will be apparent from the following description, only registration marker 40 is subject to fluoroscopy, and patient marker 38 is not subject to fluoroscopy.

Also during the initial stage of the procedure, a camera 42 is used to image the registration marker and the patient marker. The camera is positioned so as to be able to image the positions of the registration marker and the patient marker, and so that neither marker occludes the other. As is explained below, the image of the registration marker and the patient marker formed by camera 42 is used to register patient marker 38 with the anatomy of patient 30. In one embodiment camera 42 is mounted on a head mounted display worn by the medical professional referred to above, for instance, on the head-mounted display 184 described with reference to FIG. 6 below. However, other arrangements for camera 42, so that as imaged by the camera neither marker occludes the other are also considered to be within the scope of the present invention.

Camera 42 typically operates in the visible and/or near-visible spectrum, i.e., at wavelengths of approximately 300 nm-900 nm.

A processing system 28 is coupled, by cables and/or wirelessly, to camera 42. System 28 comprises a computer processor 32, a screen 34, and an input device 36 such as a pointing device, and the system is configured to analyze the images acquired by the camera, as is described further below. Other functions of system 28 are also described below.

FIGS. 2 and 3 are respectively schematic perspective and cross-sectional views of registration marker 40, which is assumed to define a registration marker frame of reference 50, herein assumed to comprise an orthogonal set of xyz axes. Marker 40 is formed from a solid substrate 44, which is opaque to light in the visible and near-visible spectrum, and which is transparent to fluoroscopic radiation. Substrate 44 is typically formed from a hard plastic, such as polycarbonate, but any other solid material which is opaque to light and transparent to fluoroscopic radiation may be used in embodiments of the present invention.

In the illustrated embodiment of marker 40, substrate 44 is formed as a rectangular parallelepiped 46, upon which is mounted a pillar 48.

A plurality of optically reflective, but radiotransparent, discrete elements 54 are disposed on substrate 44. Elements 54 are hereinbelow, by way of example, assumed to comprise discs, and are also referred to herein as discs 54. It is understood that said optically reflective and radiotransparent elements may be of different shapes and/or sizes.

Some of the plurality of discs 54 are fixedly attached, typically by cementing, to a two-dimensional (2D) surface 52 of parallelepiped 46. These discs 54 are formed in a generally rectangular 2D pattern on surface 52. In addition, an optically reflective disc 54 is also cemented onto pillar 48, so that there is in totality a three-dimensional (3D) array of discs 54 disposed on the substrate. The 3D array of discs 54 are distributed on 2D surface 52, and on pillar 48, so that when marker 40 is illuminated and imaged by camera 50 the discs are easily distinguished from substrate 44. Furthermore, as explained in more detail below, the arrangement of discs 54 are configured to enable processor 32 to unambiguously determine the orientation and position of frame of reference 50 from the marker image.

The distributed discs 54 are herein assumed to comprise an optical component 56 of marker 40 that forms an optical pattern 58 for the marker. In a particular aspect of the invention optical pattern 58, comprising the distribution of discs 54, is implemented so that the pattern has no axis of symmetry and no plane of symmetry. The absence of both an axis and a plane of symmetry in the pattern ensures that the unambiguous determination of the orientation and position of the frame of reference of marker 40 is possible from the marker image for multiple different orientations and positions of the marker, the positions being typically within a region approximately 20 cm from the patient marker.

The description above of optical pattern 58 assumes that discs 54 are configured in three dimensions. However, as long as the pattern has no axis of symmetry and no plane of symmetry, the discs forming the pattern may be arranged in only two dimensions, for example, absent the disc on pillar 48. Thus, pattern 58 may be formed in at least two dimensions, i.e., in the case of discs 54, as a two-dimensional array of the discs or as a three-dimensional array of the discs.

It will be understood that the requirement for discs 54 to be arranged to form a pattern having an absence of both an axis and a plane of symmetry may be achieved using discs of substantially the same size and shape, wherein locations of the discs are selected so that the locations are arranged to have the absence of both an axis and a plane of symmetry. The described pattern is hereinbelow referred to as a unique optical pattern.

Alternatively, the unique optical pattern may be achieved using discs of different sizes and/or shapes. In this case, the locations of the discs may also satisfy the requirement, but this is not a necessity.

A multiplicity of radiopaque elements 60 are disposed in substrate 44 by being embedded in a distribution within parallelepiped 46. The distribution of elements 60 is arranged in a two dimensional radiopaque pattern 62 such that, as for the pattern of discs 54, the radiopaque pattern has no axis of symmetry and no plane of symmetry. Because substrate 44 is radiotransparent, and because of the absence of both an axis and a plane of symmetry in radiopaque pattern 62, a fluoroscopic, typically computerized tomography (CT), scan of the radiopaque elements of marker 40 enables the orientation and position of frame of reference 50 to be unambiguously determined by processor 32 from the fluoroscopic scan. In one embodiment elements 60 comprise spheres which are distributed in a 2D generally rectangular 2D pattern that is substantially the same as the rectangular pattern of discs 54 on surface 52.

The description above of elements 60 assumes that they are arranged in a radiopaque pattern of two dimensions. However, as long as the pattern has no axis of symmetry and no plane of symmetry, the elements forming the pattern may also be arranged in three dimensions, for example, by incorporation of a radiopaque element 60A, substantially similar to elements 60, in pillar 48. Thus, pattern 62 may also be formed in at least two dimensions, i.e., in the case of elements 60 and 60A, as a two-dimensional array of elements 60 or as a three-dimensional array of elements 60 and 60A.

As for discs 54, it will be understood that the requirement for elements 60 to be arranged to form a pattern having an absence of both an axis and a plane of symmetry may be achieved using elements of substantially the same size and shape, wherein locations of the elements are selected so that the locations are arranged to have the absence of both an axis and a plane of symmetry. The described pattern is hereinbelow referred to as a unique radiopaque pattern.

Alternatively, the unique radiopaque pattern may be achieved using elements of different sizes and/or shapes. In this case, the locations of the elements may also satisfy the requirement, but this is not a necessity.

The X-ray wavelengths of the CT scan are assumed to be in a range of 0.01-10 nm.

The above description of marker 40 assumes that discs 54 and elements 60 have different functionalities—the discs being optically reflective and radiotransparent, and the elements being radiopaque. In an alternative embodiment of marker 40 at least some of discs 54 are configured to have dual functionality by being optically reflective and radiopaque. As for the embodiment described above, in the alternative embodiment discs 54 are configured and distributed on substrate 44 so that an optical image of marker 40 provides an unambiguous determination of the orientation and position of frame of reference 50, and a fluoroscopic scan of the marker also provides an unambiguous determination of the orientation and position of the frame of reference.

The physical construction of the illustrated embodiment of marker 40, as a pillar attached to a rectangular parallelepiped, comprising an array of discs 54 and an array of elements 60, is but one example of possible physical constructions of the marker that enables an unambiguous determination of the marker's position and orientation from a camera image and from a fluoroscopic scan. In a disclosed embodiment, rather than marker 40 comprising pillar 48 mounted on substrate 44, an indentation (in place of the pillar) is formed within the substrate, and a disc 54 is located on a surface of the indentation.

Other suitable constructions for marker 40 are also considered to be within the scope of the present invention.

For example, the substrate of marker 40, rather than being formed from a parallelepiped with a pillar or an indentation, may be formed as substantially any conveniently shaped solid object that is opaque to light in the visible and near-visible spectrum and which is transparent to fluoroscopic radiation.

In addition, rather than the optical component of marker 40 being comprised of a plurality of discs 54 arranged in a particular pattern, the component may comprise any array or pattern of optical elements that is attached to the substrate, that is diffusely and/or specularly reflective, and that is configured to have the absence of axes and planes of symmetry described above, so that when imaged in visible or near-visible light an unambiguous determination of the marker's position and orientation may be made.

Referring to FIG. 4, patient marker 38 is assumed to define a patient marker frame of reference 100, assumed to comprise an orthogonal set of xyz axes. In the embodiment illustrated in FIG. 4 marker 38 comprises a rectangular parallelepiped substrate 102 to which is attached a tongue 104 used to fixedly connect the substrate to clamp 30. The connection to clamp 30 is by a removable screw 112, and the patient marker connects in a predetermined fixed spatial relationship to the clamp using holes 114 which align with studs 116 of the clamp. Substrate 102 comprises a solid opaque material, and may be formed from any convenient material such as polyimide plastic.

In some embodiments, patient marker 38 may be connected to clamp 30 in more than one fixed spatial relationship. For example, in the embodiment illustrated in FIG. 4, marker 38 may be removed from the clamp, and then reattached to the clamp using screw 112 after being rotated 180° around an axis parallel to the illustrated z axis. It will be understood that holes 114 and mating studs 116 accommodate the two possible fixed spatial relationships. Other mechanical arrangements allowing for the connection of marker 38 to clamp 30 in a plurality of predetermined fixed spatial relationships are assumed to be comprised within the scope of the present invention.

A plurality of optically reflective discs 106, generally similar to discs 54, are attached, typically by cementing, to an upper 2D surface 110 of substrate 102. Discs 106 are formed in a generally rectangular 2D pattern on surface 110. Discs 106 are distributed so that when illuminated and imaged by camera 42 they are easily distinguished from substrate 102, and so that an optical pattern 118 formed by the discs enables processor 32 to unambiguously determine the orientation and position of frame of reference 100 from the camera image. As for discs 54, discs 106 are typically distributed so that they have no axis or plane of symmetry.

In FIG. 4 discs 106 are shown as being distributed on sides of a rectangle, however, it will be understood that this is but one example for the positioning of the discs on surface 110. Other distributions of discs 106 providing, from their images, unambiguous determination of the orientation and position of frame of reference 100 are also assumed to be comprised within the scope of the present invention.

Furthermore, it will be appreciated that the physical construction of patient marker 38 described above is by way of example. Thus, embodiments of the present invention comprise any patient marker formed of any conveniently shaped solid opaque substrate to which is attached an optical pattern, the pattern enabling processor 32 to unambiguously determine the orientation and position of a frame of reference of the marker from a camera image of the optical pattern. As for the example described above with reference to FIG. 4, such a patient marker may be configured to be attached to clamp 30 in a plurality of predetermined fixed spatial relationships with the clamp.

Figure 5:
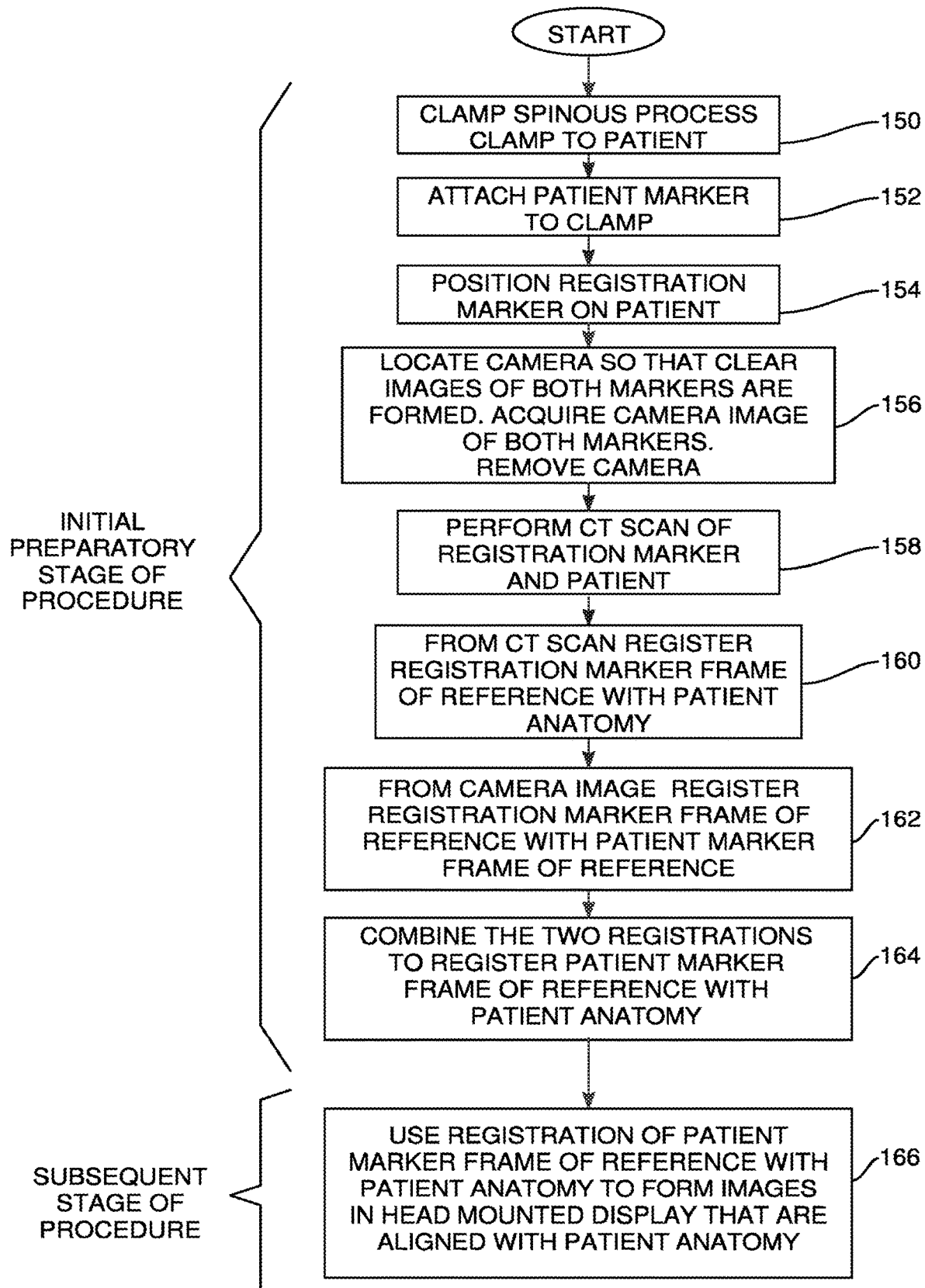
FIG. 5 is a flowchart of steps performed to register a patient marker with the anatomy of a patient during the initial preparatory stage.
Figure 6:
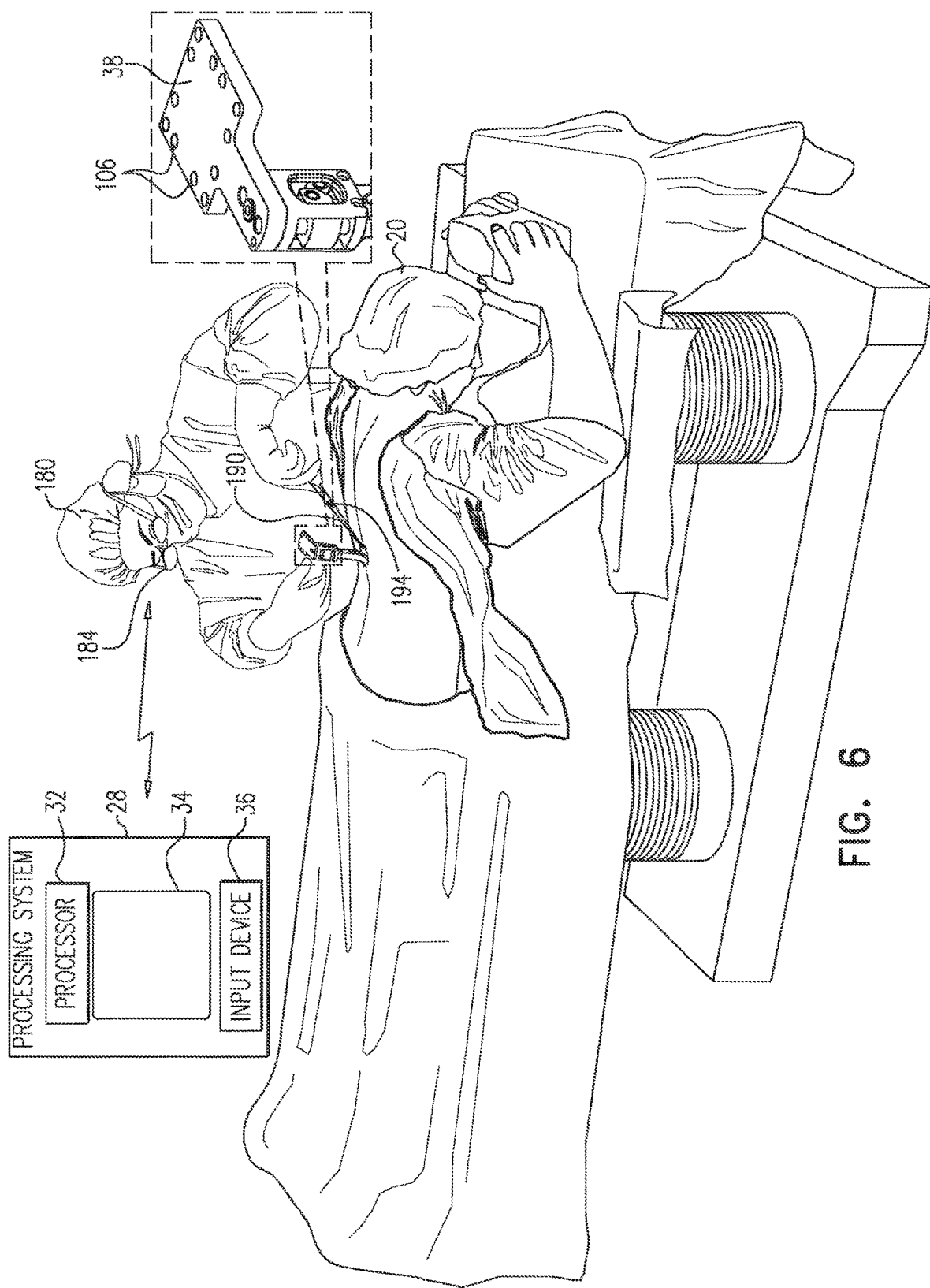
FIG. 6 is a schematic illustration of a subsequent stage of the procedure, according to an embodiment of the present invention.

FIG. 5 is a flowchart of steps performed to register patient marker 38 with the anatomy of patient 20 during the initial preparatory stage of a medical procedure, and FIG. 6 is a schematic illustration of a subsequent stage of the procedure, according to an embodiment of the present invention. Except as otherwise stated, in the following description the steps of the flowchart are assumed to be performed during the initial preparatory stage of the medical procedure, as described above. In addition, while the following description assumes a CT scan, other types of fluoroscopic imaging are also considered to be within the scope of the present invention.

In an initial step 150, a medical professional makes an incision in the back of patient 20, inserts spinous clamp 30 into the patient, and then clamps the clamp to one or more of the processes of the patient.

In a patient marker step 152, the medical professional attaches patient marker 38 to spinous clamp 30, ensuring that the marker is rigidly attached to the clamp.

In a registration marker step 154, the professional places registration marker 40 on the skin of the back of the patient, typically as close to the patient's spine as is convenient.

In a camera step 156, camera 42 images the registration marker and the patient marker. The camera is positioned so that the images it forms of the registration marker and of the patient marker are clear images, i.e., that neither markers occlude the other. If necessary, the professional may adjust the position of the camera (which may be mounted on head-mounted display 184) and/or the registration marker so that clear and acceptable images of both markers are acquired. Typically processor 32 of processing system 28 is configured to verify the acceptability of the two marker images, and if necessary the professional may use and communicate with system 28 to adjust, in an iterative manner, the positions of the camera and the registration marker until system 28 provides an indication to the professional that acceptable images are being generated.

Once acceptable images are being generated, a camera image of the two markers is acquired, and is provided to processing system 28. Camera 42 may then be removed from proximity to patient 20.

In a fluoroscopic scan step 158, a CT scan of patient 20, in the vicinity of marker 40 is performed, and processing system 28 acquires the scan. The scan may be performed by inserting patient 20 into a CT scanning system so that marker 40 is scanned. The insertion may be implemented by bringing the CT scanning system to patient 20, or by transporting the patient to the system. In either case, marker 40 remains in the marker's position of step 156.

In a scan analysis step 160, processor 32 analysis the CT scan acquired in step 158, the scan comprising an image of radiopaque elements 60 and of the anatomy of patient 20. From the acquired image, processor 32 calculates the position and orientation of registration marker frame of reference 50, and registers the frame of reference with the anatomy of the patient. The registration typically comprises a set of vectors P between selected points on registration marker 40 and selected vertebrae of patient 20. In one embodiment, the registration comprises using a 4×4 homogenous transformation, comprising a 3×3 rotation and a 1×3 translation, that transforms a point in the space of patient 20 to a point in registration marker frame of reference 50.

In a camera image analysis step 162, processor 32 analyzes the camera image of patient marker 38 and registration marker 40 acquired in step 156. From the acquired image, processor 32 calculates the position and orientation of registration marker frame of reference 50, and the position and orientation of patient marker frame of reference 36. Once the processor has calculated the positions and orientations of the two frames of reference, it formulates a registration of the two frames of reference as a set of vectors Q describing the transformation of the registration marker frame of reference to the patient marker frame of reference.

In a concluding analysis step 164, the processor adds the two sets of vectors found in steps 160 and 162 to formulate a registration set of vectors R between the patient marker frame of reference 36 and the patient anatomy, as shown in equation (1):

$$R = P + Q \qquad (1)$$

Step 164 is the concluding step of the initial preparatory stage of the medical procedure referred to above.

FIG. 6 illustrates a subsequent stage of the medical procedure, corresponding to a final step 166 of the flowchart. In the subsequent stage, i.e., during the final step, registration marker 40 has been removed from the back of patient 20, and a medical professional 180 operates on the patient. Professional 180 wears an augmented reality head-mounted display (HMD) 184, which is configured to present stored images, that are aligned with the patient, to the professional. In order to operate, HMD 184 is coupled to processor 32 of system 28, or alternatively HMD 184 has its own dedicated processor which performs similar functions to those performed by processor 32.

To perform the alignment for HMD 184, the HMD projects visible or invisible light to patient marker 38, and acquires images of reflectors 106 of the marker. From the acquired images, the HMD processor determines the position and orientation of frame of reference 100 of the patient marker. The processor applies the registration set of vectors R, found in step 164, to the position and orientation of the marker frame of reference in order to ensure that the images projected by the HMD align with the anatomy of patient 20.

In some embodiments of the present invention, during step 166 one or more surgical tools used by professional 180 are tracked by the processor of HMD 184. By way of example, FIG. 6 illustrates a surgical tool 190 used by the professional, and the tool is tracked by the HMD processor, by having identifying reflectors 194, generally similar to reflectors 106, attached to the tool. From the tracking of the tool, the HMD processor is able to present an image of the tool (on HMD 184) that aligns with the actual tool, and the image may effectively make visible to the professional elements of the actual tool that may be hidden by the patient's anatomy.

During step 166 there may be situations where the positioning of patient marker 38 interferes with the actions of professional 180. Embodiments of the present invention accommodate this type of interference, by allowing the patient marker to be removed from clamp 30, and reattached in a different predetermined fixed spatial relationship with the clamp. Such a removal and reattachment of the marker with a rotation of 180° is described above with reference to FIG. 4, and the scope of the present invention includes removal and reattachment of the marker in any one of a plurality predetermined fixed spatial relationships.

In the case of embodiments comprising such a plurality predetermined fixed spatial relationships, processor 32 is configured, typically prior to implementation of step 166, to recognize the changed relationship of the patient marker with the clamp, and to compensate for the changed relationship.

An augmented reality head mounted display such as HMD 184 is described in more detail in U.S. Patent Application 2017/0178375 which is incorporated herein by reference. The application also describes making visible to a professional elements of an actual tool, used in a medical procedure, that may be hidden by the patient's anatomy.

In the description herein and in the claims, an entity having no axis of symmetry is assumed to have no rotational axis of symmetry other than a trivial rotational axis of symmetry of 360° or an integral multiple thereof. Also in the description herein and in the claims, a two dimensional entity having no plane of symmetry is assumed to have no mirror plane of symmetry other than a trivial mirror plane wherein the two dimensional entity lies.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

What is claimed is:

1. A method of manufacturing a registration marker, the method comprising:
   providing a radiotransparent substrate;
   disposing an optically visible pattern formed in at least two dimensions on the radiotransparent substrate; and
   disposing in the radiotransparent substrate a multiplicity of radiopaque elements, the radiopaque elements being spatially arranged in at least two dimensions to provide a radiopaque pattern that provides a position and frame of reference of the registration marker,
   wherein the radiotransparent substrate is optically opaque and comprises a surface, and wherein the optically visible pattern is disposed on the surface,
   wherein the optically visible pattern comprises optically reflective discrete elements fixedly mounted on the surface, and
   wherein the optically reflective discrete elements are different from the radiopaque elements.

2. The method according to claim 1, wherein the optically visible pattern has no axis of symmetry and no plane of symmetry.

3. The method according to claim 1, wherein the radiotransparent substrate comprises a pillar attached to a rectangular parallelepiped, and wherein one of the optically reflective discrete elements is mounted on the pillar.

4. The method according to claim 1, wherein the radiotransparent substrate comprises an indentation formed within a rectangular parallelepiped, and wherein one of the optically reflective discrete elements is mounted on a surface of the indentation.

5. The method according to claim 1, wherein the optically visible pattern is formed in two dimensions.

6. The method according to claim 1, wherein the optically visible pattern is formed in three dimensions.

7. The method according to claim 1, wherein the radiopaque elements are spatially arranged in two dimensions.

8. The method according to claim 1, wherein the radiopaque elements are spatially arranged in three dimensions.

9. The method according to claim 8, wherein the radiopaque elements comprise spheres.

10. The method according to claim 1, wherein the radiopaque pattern has no axis of symmetry and no plane of symmetry.

11. The method according to claim 1, wherein the optically reflective discrete elements comprise discs.

12. A method of manufacturing a registration marker, the method comprising:
    disposing a plurality of optically reflective, radiotransparent, discrete elements in at least two dimensions on a radiotransparent substrate to form an optical pattern for the registration marker; and
    disposing in the radiotransparent substrate a plurality of radiopaque elements, the radiopaque elements being spatially arranged in at least two dimensions to provide a radiopaque pattern that provides a position and frame of reference of the registration marker
    wherein the plurality of optically reflective, radiotransparent, discrete elements are different from the plurality of radiopaque elements.

13. The method of claim 12, wherein disposing the plurality of optically reflective, radiotransparent, discrete elements in at least two dimensions on the radiotransparent substrate comprises fixedly mounting the plurality of optically reflective, radiotransparent, discrete elements on the radiotransparent substrate.

14. The method of claim 12, wherein the plurality of optically reflective, radiotransparent, discrete elements comprise discs.

15. The method of claim 12, wherein the optical pattern is formed in three dimensions.

16. The method of claim 15, wherein the optical pattern has no axis of symmetry and no plane of symmetry.

17. The method of claim 12, wherein the plurality of radiopaque elements are spatially arranged in three dimensions.

18. The method of claim 17, wherein the radiopaque pattern has no axis of symmetry and no plane of symmetry.

* * * * *